United States Patent
Bachmann et al.

(10) Patent No.: US 10,471,199 B2
(45) Date of Patent: Nov. 12, 2019

(54) GRAPHENE-BASED FILTER FOR ISOLATING A SUBSTANCE FROM BLOOD

(71) Applicant: Lockheed Martin Corporation, Bethesda, MD (US)

(72) Inventors: Svetlana Monakhova Bachmann, Liverpool, NY (US); Paul Declan Mountcastle, Moorestown, NJ (US); Byron W. Tietjen, Baldwinsville, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 140 days.

(21) Appl. No.: 15/410,457

(22) Filed: Jan. 19, 2017

(65) Prior Publication Data

US 2017/0128891 A1    May 11, 2017

Related U.S. Application Data

(63) Continuation of application No. 13/923,503, filed on Jun. 21, 2013, now Pat. No. 9,572,918.

(51) Int. Cl.
*A61M 1/34* (2006.01)
*B01D 71/02* (2006.01)
(Continued)

(52) U.S. Cl.
CPC .............. *A61M 1/34* (2013.01); *A61K 35/14* (2013.01); *A61M 1/1631* (2014.02); *A61M 1/36* (2013.01);
(Continued)

(58) Field of Classification Search
CPC ....... A61K 35/14; A61M 1/1631; A61M 1/34; A61M 1/36; A61M 1/3633;
(Continued)

(56) References Cited

U.S. PATENT DOCUMENTS

| 2,187,417 A | 1/1940 | Doble |
| 3,024,153 A | 3/1962 | Kennedy |

(Continued)

FOREIGN PATENT DOCUMENTS

| CA | 2037988 | 9/1992 |
| CA | 2411935 | 12/2002 |

(Continued)

OTHER PUBLICATIONS

Adiga et al., "Nanoporous Materials for Biomedical Devices," JOM 60: 26-32 (Mar. 25, 2008).

(Continued)

*Primary Examiner* — John Kim
(74) *Attorney, Agent, or Firm* — Foley & Lardner LLP

(57) ABSTRACT

A device isolates a substance from blood. The substance includes particles with an effective diameter that is within a range defined by effective diameters of constituents of blood. The device comprises a first sheet of graphene including a first plurality of apertures. The first plurality of apertures are configured to pass objects with an effective diameter less than or equal to the effective diameter of the particles of the substance. The device comprises a second sheet of graphene including a second plurality of apertures. The second plurality of apertures are configured to pass objects with an effective diameter less than the effective diameter of the particles of the substance. The device may be configured to include a conduit system. The device may be configured to operate according to a reversible cycle.

14 Claims, 6 Drawing Sheets

(51) Int. Cl.
*A61M 1/36* (2006.01)
*B01D 61/02* (2006.01)
*B01D 69/12* (2006.01)
*A61K 35/14* (2015.01)
*A61M 1/16* (2006.01)
*B01D 69/02* (2006.01)

(52) U.S. Cl.
CPC ........... *A61M 1/3633* (2013.01); *B01D 61/02* (2013.01); *B01D 69/02* (2013.01); *B01D 69/12* (2013.01); *B01D 71/021* (2013.01); *A61M 2202/0014* (2013.01); *A61M 2202/0042* (2013.01); *A61M 2205/04* (2013.01); *B01D 2325/02* (2013.01)

(58) Field of Classification Search
CPC .. A61M 2202/0014; A61M 2202/0042; A61M 2205/04; B01D 2325/02; B01D 61/02; B01D 69/02; B01D 69/12; B01D 71/021
See application file for complete search history.

(56) References Cited

U.S. PATENT DOCUMENTS

| | | |
|---|---|---|
| 3,303,085 A | 2/1967 | Price et al. |
| 3,501,831 A | 3/1970 | Gordon |
| 3,593,854 A | 7/1971 | Swank |
| 3,692,059 A | 9/1972 | Ice, Jr. |
| 3,701,433 A | 10/1972 | Krakauer et al. |
| 3,802,972 A | 4/1974 | Fleischer et al. |
| 3,896,733 A | 7/1975 | Rosenberg |
| 4,043,331 A | 8/1977 | Martin et al. |
| 4,073,732 A | 2/1978 | Lauer et al. |
| 4,159,954 A | 7/1979 | Gangemi |
| 4,162,220 A | 7/1979 | Servas |
| 4,277,344 A | 7/1981 | Cadotte |
| 4,303,530 A | 12/1981 | Shah et al. |
| 4,457,747 A | 7/1984 | Tu |
| 4,743,371 A | 5/1988 | Servas et al. |
| 4,804,363 A | 2/1989 | Valeri |
| 4,855,058 A | 8/1989 | Holland et al. |
| 4,880,440 A | 11/1989 | Perrin |
| 4,889,626 A | 12/1989 | Browne |
| 4,891,134 A | 1/1990 | Vcelka |
| 4,925,560 A | 5/1990 | Sorrick |
| 4,935,207 A | 6/1990 | Stanbro et al. |
| 4,976,858 A | 12/1990 | Kadoya |
| 5,052,444 A | 10/1991 | Messerly et al. |
| 5,080,770 A | 1/1992 | Culkin |
| 5,082,476 A | 1/1992 | Kahlbaugh et al. |
| 5,156,628 A | 10/1992 | Kranz |
| 5,182,111 A | 1/1993 | Aebischer et al. |
| 5,185,086 A | 2/1993 | Kaali et al. |
| 5,201,767 A | 4/1993 | Caldarise et al. |
| 5,244,981 A | 9/1993 | Seidner et al. |
| 5,277,748 A | 1/1994 | Sakaguchi et al. |
| 5,314,492 A | 5/1994 | Hamilton et al. |
| 5,314,960 A | 5/1994 | Spinelli et al. |
| 5,314,961 A | 5/1994 | Anton et al. |
| 5,331,067 A | 7/1994 | Seidner et al. |
| 5,344,454 A | 9/1994 | Clarke et al. |
| 5,371,147 A | 12/1994 | Spinelli et al. |
| 5,425,858 A | 6/1995 | Farmer |
| 5,480,449 A | 1/1996 | Hamilton et al. |
| 5,514,181 A | 5/1996 | Light et al. |
| 5,516,522 A | 5/1996 | Peyman et al. |
| 5,549,697 A | 8/1996 | Caldarise |
| 5,562,944 A | 10/1996 | Kafrawy |
| 5,565,210 A | 10/1996 | Rosenthal et al. |
| 5,580,530 A | 12/1996 | Kowatsch et al. |
| 5,595,621 A | 1/1997 | Light et al. |
| 5,636,437 A | 6/1997 | Kaschmitter et al. |
| 5,639,275 A | 6/1997 | Baetge et al. |
| 5,641,323 A | 6/1997 | Caldarise |
| 5,658,334 A | 8/1997 | Caldarise et al. |
| 5,662,158 A | 9/1997 | Caldarise |
| 5,665,118 A | 9/1997 | Lasalle et al. |
| 5,671,897 A | 9/1997 | Ogg et al. |
| 5,679,232 A | 10/1997 | Fedor et al. |
| 5,679,249 A | 10/1997 | Fendya et al. |
| 5,687,788 A | 11/1997 | Caldarise et al. |
| 5,700,477 A | 12/1997 | Rosenthal et al. |
| 5,713,410 A | 2/1998 | Lasalle et al. |
| 5,716,412 A | 2/1998 | DeCarlo et al. |
| 5,716,414 A | 2/1998 | Caldarise |
| 5,725,586 A | 3/1998 | Sommerich |
| 5,725,775 A | 3/1998 | Bene et al. |
| 5,731,360 A | 3/1998 | Pekala et al. |
| 5,733,503 A | 3/1998 | Kowatsch et al. |
| 5,746,272 A | 5/1998 | Mastrorio et al. |
| 5,782,286 A | 7/1998 | Sommerich |
| 5,782,289 A | 7/1998 | Mastrorio et al. |
| 5,788,916 A | 8/1998 | Caldarise |
| 5,800,828 A | 9/1998 | Dionne et al. |
| 5,808,312 A | 9/1998 | Fukuda |
| 5,868,727 A | 2/1999 | Barr et al. |
| 5,897,592 A | 4/1999 | Caldarise et al. |
| 5,902,762 A | 5/1999 | Mercuri et al. |
| 5,906,234 A | 5/1999 | Mastrorio et al. |
| 5,910,172 A | 6/1999 | Penenberg |
| 5,910,173 A | 6/1999 | Decarlo et al. |
| 5,913,998 A | 6/1999 | Butler et al. |
| 5,922,304 A | 7/1999 | Unger |
| 5,925,247 A | 7/1999 | Huebbel |
| 5,932,185 A | 8/1999 | Pekala et al. |
| 5,935,084 A | 8/1999 | Southworth |
| 5,935,172 A | 8/1999 | Ochoa et al. |
| 5,954,937 A | 9/1999 | Farmer |
| 5,974,973 A | 11/1999 | Tittgemeyer |
| 5,976,555 A | 11/1999 | Liu et al. |
| 5,980,718 A | 11/1999 | Van Konynenburg et al. |
| 6,008,431 A | 12/1999 | Caldarise et al. |
| 6,013,080 A | 1/2000 | Khalili |
| 6,022,509 A | 2/2000 | Matthews et al. |
| 6,052,608 A | 4/2000 | Young et al. |
| 6,080,393 A | 6/2000 | Liu et al. |
| 6,093,209 A | 7/2000 | Sanders |
| 6,139,585 A | 10/2000 | Li |
| 6,152,882 A | 11/2000 | Prutchi |
| 6,156,323 A | 12/2000 | Verdicchio et al. |
| 6,193,956 B1 | 2/2001 | Liu et al. |
| 6,209,621 B1 | 4/2001 | Treacy |
| 6,213,124 B1 | 4/2001 | Butterworth |
| 6,228,123 B1 | 5/2001 | Dezzani |
| 6,264,699 B1 | 7/2001 | Noiles et al. |
| 6,292,704 B1 | 9/2001 | Malonek et al. |
| 6,309,532 B1 | 10/2001 | Tran et al. |
| 6,346,187 B1 | 2/2002 | Tran et al. |
| 6,375,014 B1 | 4/2002 | Garcera et al. |
| 6,423,022 B1 | 7/2002 | Roeher et al. |
| 6,426,214 B1 | 7/2002 | Butler et al. |
| 6,454,095 B1 | 9/2002 | Brisebois et al. |
| 6,455,115 B1 | 9/2002 | Demeyer |
| 6,461,622 B2 | 10/2002 | Liu et al. |
| 6,462,935 B1 | 10/2002 | Shiue et al. |
| 6,521,865 B1 | 2/2003 | Jones et al. |
| 6,532,386 B2 | 3/2003 | Sun et al. |
| 6,544,316 B2 | 4/2003 | Baker et al. |
| 6,580,598 B2 | 6/2003 | Shiue et al. |
| 6,654,229 B2 | 11/2003 | Yanagisawa et al. |
| 6,659,298 B2 | 12/2003 | Wong |
| 6,660,150 B2 | 12/2003 | Conlan et al. |
| 6,661,643 B2 | 12/2003 | Shiue et al. |
| 6,686,437 B2 | 2/2004 | Buchman et al. |
| 6,692,627 B1 | 2/2004 | Russell et al. |
| 6,695,880 B1 | 2/2004 | Roffman et al. |
| 6,699,684 B2 | 3/2004 | Ho et al. |
| 6,719,740 B2 | 4/2004 | Burnett et al. |
| 6,905,612 B2 | 6/2005 | Dorian et al. |
| 6,924,190 B2 | 8/2005 | Dennison |
| 7,014,829 B2 | 3/2006 | Yanagisawa et al. |
| 7,071,406 B2 | 7/2006 | Smalley et al. |
| 7,092,753 B2 | 8/2006 | Darvish et al. |
| 7,138,042 B2 | 11/2006 | Tran et al. |

(56) References Cited

U.S. PATENT DOCUMENTS

| | | |
|---|---|---|
| 7,171,263 B2 | 1/2007 | Darvish et al. |
| 7,175,783 B2 | 2/2007 | Curran |
| 7,179,419 B2 | 2/2007 | Lin et al. |
| 7,190,997 B1 | 3/2007 | Darvish et al. |
| 7,267,753 B2 | 9/2007 | Anex et al. |
| 7,306,768 B2 | 12/2007 | Chiga |
| 7,357,255 B2 | 4/2008 | Ginsberg et al. |
| 7,374,677 B2 | 5/2008 | McLaughlin et al. |
| 7,381,707 B2 | 6/2008 | Lin et al. |
| 7,382,601 B2 | 6/2008 | Yoshimitsu |
| 7,434,692 B2 | 10/2008 | Ginsberg et al. |
| 7,452,547 B2 | 11/2008 | Lambino et al. |
| 7,459,121 B2 | 12/2008 | Liang et al. |
| 7,460,907 B1 | 12/2008 | Darvish et al. |
| 7,476,222 B2 | 1/2009 | Sun et al. |
| 7,477,939 B2 | 1/2009 | Sun et al. |
| 7,477,940 B2 | 1/2009 | Sun et al. |
| 7,477,941 B2 | 1/2009 | Sun et al. |
| 7,479,133 B2 | 1/2009 | Sun et al. |
| 7,505,250 B2 | 3/2009 | Cho et al. |
| 7,531,094 B2 | 5/2009 | McLaughlin et al. |
| 7,600,567 B2 | 10/2009 | Christopher et al. |
| 7,631,764 B2 | 12/2009 | Ginsberg et al. |
| 7,650,805 B2 | 1/2010 | Nauseda et al. |
| 7,674,477 B1 | 3/2010 | Schmid et al. |
| 7,706,128 B2 | 4/2010 | Bourcier |
| 7,732,301 B1 | 6/2010 | Pinnington et al. |
| 7,761,809 B2 | 7/2010 | Bukovec et al. |
| 7,786,086 B2 | 8/2010 | Reches et al. |
| 7,866,475 B2 | 1/2011 | Doskoczynski et al. |
| 7,875,293 B2 | 1/2011 | Shults et al. |
| 7,935,331 B2 | 5/2011 | Lin |
| 7,935,416 B2 | 5/2011 | Yang et al. |
| 7,943,167 B2 | 5/2011 | Kulkarni et al. |
| 7,960,708 B2 | 6/2011 | Wolfe et al. |
| 7,998,246 B2 | 8/2011 | Liu et al. |
| 8,109,893 B2 | 2/2012 | Lande |
| 8,147,599 B2 | 4/2012 | McAlister |
| 8,262,943 B2 | 9/2012 | Meng et al. |
| 8,278,106 B2 | 10/2012 | Martinson et al. |
| 8,308,702 B2 | 11/2012 | Batchvarova et al. |
| 8,316,865 B2 | 11/2012 | Ochs et al. |
| 8,329,476 B2 | 12/2012 | Pitkanen et al. |
| 8,354,296 B2 | 1/2013 | Dimitrakopoulos et al. |
| 8,361,321 B2 | 1/2013 | Stetson et al. |
| 8,449,504 B2 | 5/2013 | Carter et al. |
| 8,471,562 B2 | 6/2013 | Knizhnik |
| 8,475,689 B2 | 7/2013 | Sun et al. |
| 8,506,807 B2 | 8/2013 | Lee et al. |
| 8,512,669 B2 | 8/2013 | Hauck |
| 8,513,324 B2 | 8/2013 | Scales et al. |
| 8,535,726 B2 | 9/2013 | Dai et al. |
| 8,592,291 B2 | 11/2013 | Shi et al. |
| 8,617,411 B2 | 12/2013 | Singh |
| 8,666,471 B2 | 3/2014 | Rogers et al. |
| 8,686,249 B1 | 4/2014 | Whitaker et al. |
| 8,697,230 B2 | 4/2014 | Ago et al. |
| 8,698,481 B2 | 4/2014 | Lieber et al. |
| 8,715,329 B2 | 5/2014 | Robinson et al. |
| 8,721,074 B2 | 5/2014 | Pugh et al. |
| 8,734,421 B2 | 5/2014 | Sun et al. |
| 8,744,567 B2 | 6/2014 | Fassih et al. |
| 8,751,015 B2 | 6/2014 | Frewin et al. |
| 8,753,468 B2 | 6/2014 | Caldwell et al. |
| 8,759,153 B2 | 6/2014 | Elian et al. |
| 8,808,257 B2 | 8/2014 | Pugh et al. |
| 8,828,211 B2 | 9/2014 | Garaj et al. |
| 8,840,552 B2 | 9/2014 | Brauker et al. |
| 8,857,983 B2 | 10/2014 | Pugh et al. |
| 8,861,821 B2 | 10/2014 | Osumi |
| 8,894,201 B2 | 11/2014 | Pugh et al. |
| 8,940,552 B2 | 1/2015 | Pugh et al. |
| 8,950,862 B2 | 2/2015 | Pugh et al. |
| 8,974,055 B2 | 3/2015 | Pugh et al. |
| 8,975,121 B2 | 3/2015 | Pugh et al. |
| 8,979,978 B2 | 3/2015 | Miller et al. |
| 8,986,932 B2 | 3/2015 | Turner et al. |
| 8,993,234 B2 | 3/2015 | Turner et al. |
| 8,993,327 B2 | 3/2015 | McKnight et al. |
| 9,014,639 B2 | 4/2015 | Pugh et al. |
| 9,017,937 B1 | 4/2015 | Turner et al. |
| 9,023,220 B2 | 5/2015 | Graphenea |
| 9,028,663 B2 | 5/2015 | Stetson et al. |
| 9,035,282 B2 | 5/2015 | Dimitrakopoulos et al. |
| 9,045,847 B2 | 6/2015 | Batchvarova et al. |
| 9,050,452 B2 | 6/2015 | Sun et al. |
| 9,052,533 B2 | 6/2015 | Pugh et al. |
| 9,056,282 B2 | 6/2015 | Miller et al. |
| 9,062,180 B2 | 6/2015 | Scales et al. |
| 9,067,811 B1 | 6/2015 | Bennett et al. |
| 9,070,615 B2 | 6/2015 | Elian et al. |
| 9,075,009 B2 | 7/2015 | Kim et al. |
| 9,080,267 B2 | 7/2015 | Batchvarova et al. |
| 9,095,821 B1 | 8/2015 | Ratto et al. |
| 9,095,823 B2 | 8/2015 | Fleming |
| 9,096,050 B2 | 8/2015 | Bedell et al. |
| 9,096,437 B2 | 8/2015 | Tour et al. |
| 9,102,111 B2 | 8/2015 | Pugh et al. |
| 9,108,158 B2 | 8/2015 | Yu et al. |
| 9,110,310 B2 | 8/2015 | Pugh et al. |
| 9,125,715 B2 | 9/2015 | Pugh et al. |
| 9,134,546 B2 | 9/2015 | Pugh et al. |
| 9,156,700 B2 | 10/2015 | Zhamu et al. |
| 9,170,646 B2 | 10/2015 | Toner et al. |
| 9,185,486 B2 | 11/2015 | Pugh |
| 9,193,587 B2 | 11/2015 | Bennett |
| 9,195,075 B2 | 11/2015 | Pugh et al. |
| 9,225,375 B2 | 12/2015 | Pugh et al. |
| 9,388,048 B1 | 7/2016 | Zhou et al. |
| 9,425,709 B2 | 8/2016 | Hayashi et al. |
| 9,437,370 B2 | 9/2016 | Chen et al. |
| 9,463,421 B2 | 10/2016 | Fleming |
| 9,475,709 B2 | 10/2016 | Stetson et al. |
| 9,505,192 B2 | 11/2016 | Stoltenberg et al. |
| 9,545,600 B2 | 1/2017 | Miller et al. |
| 9,567,224 B2 | 2/2017 | Bedworth |
| 9,572,918 B2 | 2/2017 | Bachmann et al. |
| 9,592,475 B2 | 3/2017 | Stoltenberg et al. |
| 9,610,546 B2 | 4/2017 | Sinton et al. |
| 9,656,214 B2 | 5/2017 | Miller et al. |
| 9,708,640 B2 | 7/2017 | Wu et al. |
| 9,713,794 B2 | 7/2017 | Choi et al. |
| 9,742,001 B2 | 8/2017 | Zhamu et al. |
| 9,744,617 B2 | 8/2017 | Bedworth et al. |
| 9,870,895 B2 | 1/2018 | Bedworth |
| 10,005,038 B2 | 6/2018 | Stetson, Jr. et al. |
| 10,017,852 B2 | 7/2018 | Heise et al. |
| 10,096,679 B1 | 10/2018 | Antunez et al. |
| 10,118,130 B2 | 11/2018 | Swett |
| 10,124,299 B2 | 11/2018 | Kim et al. |
| 10,130,919 B1 | 11/2018 | Saleh |
| 2001/0036556 A1 | 11/2001 | Jen |
| 2001/0047157 A1 | 11/2001 | Burnett et al. |
| 2001/0055597 A1 | 12/2001 | Liu et al. |
| 2002/0079004 A1 | 6/2002 | Sato et al. |
| 2002/0079054 A1 | 6/2002 | Nakatani |
| 2002/0104435 A1 | 8/2002 | Baker et al. |
| 2002/0115957 A1 | 8/2002 | Sun et al. |
| 2002/0117659 A1 | 8/2002 | Lieber et al. |
| 2002/0183682 A1 | 12/2002 | Darvish et al. |
| 2002/0183686 A1 | 12/2002 | Darvish et al. |
| 2003/0052354 A1 | 3/2003 | Dennison |
| 2003/0134281 A1 | 7/2003 | Evans |
| 2003/0138777 A1 | 7/2003 | Evans |
| 2003/0146221 A1 | 8/2003 | Lauer et al. |
| 2003/0159985 A1 | 8/2003 | Siwy et al. |
| 2003/0171053 A1 | 9/2003 | Sanders |
| 2004/0018583 A1 | 1/2004 | Ho et al. |
| 2004/0035787 A1 | 2/2004 | Tanga et al. |
| 2004/0061253 A1 | 4/2004 | Kleinmeyer et al. |
| 2004/0063097 A1 | 4/2004 | Evans |
| 2004/0099324 A1 | 5/2004 | Fraser et al. |
| 2004/0111968 A1 | 6/2004 | Day et al. |
| 2004/0112865 A1 | 6/2004 | McCullough et al. |

(56) References Cited

U.S. PATENT DOCUMENTS

| | | |
|---|---|---|
| 2004/0121488 A1 | 6/2004 | Chang et al. |
| 2004/0140041 A1 | 7/2004 | Glick |
| 2004/0142463 A1 | 7/2004 | Walker et al. |
| 2004/0185730 A1 | 9/2004 | Lambino et al. |
| 2004/0193043 A1 | 9/2004 | Duchon et al. |
| 2004/0199243 A1 | 10/2004 | Yodfat |
| 2004/0208796 A1 | 10/2004 | Chiga |
| 2004/0217036 A1 | 11/2004 | Ginsberg et al. |
| 2004/0241214 A1 | 12/2004 | Kirkwood et al. |
| 2004/0251136 A1 | 12/2004 | Lean et al. |
| 2005/0004508 A1 | 1/2005 | Sun et al. |
| 2005/0004509 A1 | 1/2005 | Sun et al. |
| 2005/0004550 A1 | 1/2005 | Sun et al. |
| 2005/0010161 A1 | 1/2005 | Sun et al. |
| 2005/0010192 A1 | 1/2005 | Sun et al. |
| 2005/0015042 A1 | 1/2005 | Sun et al. |
| 2005/0053563 A1 | 3/2005 | Manissier et al. |
| 2005/0112078 A1 | 5/2005 | Boddupalli et al. |
| 2005/0126966 A1 | 6/2005 | Tanida et al. |
| 2005/0129633 A1 | 6/2005 | Lin |
| 2005/0148996 A1 | 7/2005 | Sun et al. |
| 2005/0170089 A1 | 8/2005 | Lashmore et al. |
| 2005/0189673 A1 | 9/2005 | Klug et al. |
| 2005/0226834 A1 | 10/2005 | Lambino et al. |
| 2005/0238730 A1 | 10/2005 | Le Fur et al. |
| 2006/0005381 A1 | 1/2006 | Nishi et al. |
| 2006/0036332 A1 | 2/2006 | Jennings |
| 2006/0073370 A1 | 4/2006 | Krusic et al. |
| 2006/0093885 A1 | 5/2006 | Krusic et al. |
| 2006/0121279 A1 | 6/2006 | Petrik |
| 2006/0151382 A1 | 7/2006 | Petrik |
| 2006/0166347 A1 | 7/2006 | Faulstich et al. |
| 2006/0180604 A1 | 8/2006 | Ginsberg et al. |
| 2006/0222701 A1 | 10/2006 | Kulkarni et al. |
| 2006/0253078 A1 | 11/2006 | Wu et al. |
| 2007/0004640 A1 | 1/2007 | Lin et al. |
| 2007/0032054 A1 | 2/2007 | Ramaswamy et al. |
| 2007/0056894 A1 | 3/2007 | Connors, Jr. |
| 2007/0060862 A1 | 3/2007 | Sun et al. |
| 2007/0062856 A1 | 3/2007 | Pahl et al. |
| 2007/0099813 A1 | 5/2007 | Luizzi et al. |
| 2007/0131646 A1 | 6/2007 | Donnelly et al. |
| 2007/0284279 A1 | 12/2007 | Doskoczynski et al. |
| 2008/0017564 A1 | 1/2008 | Hammond |
| 2008/0035484 A1 | 2/2008 | Wu et al. |
| 2008/0035541 A1 | 2/2008 | Franzreb et al. |
| 2008/0045877 A1 | 2/2008 | Levin et al. |
| 2008/0061477 A1 | 3/2008 | Capizzo |
| 2008/0063585 A1 | 3/2008 | Smalley et al. |
| 2008/0081323 A1 | 4/2008 | Keeley et al. |
| 2008/0081362 A1 | 4/2008 | Keeley et al. |
| 2008/0149561 A1 | 6/2008 | Chu et al. |
| 2008/0156648 A1 | 7/2008 | Dudziak et al. |
| 2008/0170982 A1 | 7/2008 | Zhang et al. |
| 2008/0185293 A1 | 8/2008 | Klose et al. |
| 2008/0188836 A1 | 8/2008 | Weber et al. |
| 2008/0190508 A1 | 8/2008 | Booth et al. |
| 2008/0241085 A1 | 10/2008 | Lin et al. |
| 2008/0268016 A1 | 10/2008 | Fang et al. |
| 2008/0290020 A1 | 11/2008 | Marand et al. |
| 2008/0290111 A1 | 11/2008 | Ginsberg et al. |
| 2009/0023572 A1 | 1/2009 | Backes et al. |
| 2009/0032475 A1 | 2/2009 | Ferrer et al. |
| 2009/0039019 A1 | 2/2009 | Raman |
| 2009/0048685 A1 | 2/2009 | Frigstad et al. |
| 2009/0075371 A1 | 3/2009 | Keeley et al. |
| 2009/0078640 A1 | 3/2009 | Chu et al. |
| 2009/0087395 A1 | 4/2009 | Lin et al. |
| 2009/0117335 A1 | 5/2009 | Iyoda et al. |
| 2009/0120873 A1 | 5/2009 | Becker et al. |
| 2009/0148495 A1 | 6/2009 | Hammer et al. |
| 2009/0176159 A1 | 7/2009 | Zhamu et al. |
| 2009/0222072 A1 | 9/2009 | Robinson et al. |
| 2009/0236295 A1 | 9/2009 | Braun et al. |
| 2009/0241242 A1 | 10/2009 | Beatty et al. |
| 2009/0283475 A1 | 11/2009 | Hylton et al. |
| 2009/0291270 A1 | 11/2009 | Zettl et al. |
| 2009/0294300 A1 | 12/2009 | Kanzius et al. |
| 2009/0306364 A1 | 12/2009 | Beer et al. |
| 2010/0000754 A1 | 1/2010 | Mann et al. |
| 2010/0016778 A1 | 1/2010 | Chattopadhyay |
| 2010/0021708 A1 | 1/2010 | Kong et al. |
| 2010/0024722 A1 | 2/2010 | Ochs et al. |
| 2010/0024838 A1 | 2/2010 | Ochs et al. |
| 2010/0025330 A1 | 2/2010 | Ratto et al. |
| 2010/0055464 A1 | 3/2010 | Sung |
| 2010/0059378 A1 | 3/2010 | Elson et al. |
| 2010/0072643 A1 | 3/2010 | Pugh et al. |
| 2010/0076553 A1 | 3/2010 | Pugh et al. |
| 2010/0098741 A1 | 4/2010 | Ranade |
| 2010/0105834 A1 | 4/2010 | Tour et al. |
| 2010/0110372 A1 | 5/2010 | Pugh et al. |
| 2010/0124564 A1 | 5/2010 | Martinson et al. |
| 2010/0127312 A1 | 5/2010 | Grebel et al. |
| 2010/0161014 A1 | 6/2010 | Lynch et al. |
| 2010/0167551 A1 | 7/2010 | Dedontney |
| 2010/0196439 A1 | 8/2010 | Beck et al. |
| 2010/0209330 A1 | 8/2010 | Golzhauser et al. |
| 2010/0209515 A1 | 8/2010 | Chantalat et al. |
| 2010/0213079 A1 | 8/2010 | Willis |
| 2010/0224555 A1 | 9/2010 | Hoek et al. |
| 2010/0228204 A1 | 9/2010 | Beatty et al. |
| 2010/0233781 A1 | 9/2010 | Bangera et al. |
| 2010/0249273 A1 | 9/2010 | Scales et al. |
| 2010/0258111 A1 | 10/2010 | Shah et al. |
| 2010/0323177 A1 | 12/2010 | Ruoff et al. |
| 2010/0327847 A1 | 12/2010 | Leiber et al. |
| 2011/0014217 A1 | 1/2011 | Fahmy et al. |
| 2011/0027599 A1 | 2/2011 | Hoek et al. |
| 2011/0037033 A1 | 2/2011 | Green et al. |
| 2011/0041519 A1 | 2/2011 | McAlister |
| 2011/0041687 A1 | 2/2011 | Diaz et al. |
| 2011/0045523 A1 | 2/2011 | Strano et al. |
| 2011/0054418 A1 | 3/2011 | Pugh et al. |
| 2011/0054576 A1 | 3/2011 | Robinson et al. |
| 2011/0056892 A1 | 3/2011 | Lancaster |
| 2011/0073563 A1 | 3/2011 | Chang et al. |
| 2011/0092054 A1 | 4/2011 | Seo et al. |
| 2011/0092949 A1 | 4/2011 | Wang |
| 2011/0100921 A1 | 5/2011 | Heinrich |
| 2011/0112484 A1 | 5/2011 | Carter et al. |
| 2011/0118655 A1 | 5/2011 | Fassih et al. |
| 2011/0120970 A1 | 5/2011 | Joo et al. |
| 2011/0124253 A1 | 5/2011 | Shah et al. |
| 2011/0132834 A1 | 6/2011 | Tomioka et al. |
| 2011/0138689 A1 | 6/2011 | Wismans |
| 2011/0139707 A1 | 6/2011 | Siwy et al. |
| 2011/0152795 A1 | 6/2011 | Aledo et al. |
| 2011/0186449 A1 | 8/2011 | Clochard et al. |
| 2011/0189440 A1 | 8/2011 | Appleby et al. |
| 2011/0201201 A1 | 8/2011 | Arnold et al. |
| 2011/0202201 A1 | 8/2011 | Matsubara |
| 2011/0253630 A1 | 10/2011 | Bakajin et al. |
| 2011/0258791 A1 | 10/2011 | Batchvarova et al. |
| 2011/0258796 A1 | 10/2011 | Batchvarova et al. |
| 2011/0262645 A1 | 10/2011 | Batchvarova et al. |
| 2011/0263912 A1 | 10/2011 | Miller et al. |
| 2011/0269920 A1 | 11/2011 | Min et al. |
| 2012/0000845 A1 | 1/2012 | Park et al. |
| 2012/0031833 A1 | 2/2012 | Ho et al. |
| 2012/0048804 A1 | 3/2012 | Stetson et al. |
| 2012/0115243 A1 | 5/2012 | Pitkanen et al. |
| 2012/0116228 A1 | 5/2012 | Okubo |
| 2012/0145548 A1 | 6/2012 | Sivan et al. |
| 2012/0148633 A1 | 6/2012 | Sun et al. |
| 2012/0162600 A1 | 6/2012 | Pugh et al. |
| 2012/0183738 A1 | 7/2012 | Zettl et al. |
| 2012/0186850 A1 | 7/2012 | Sugiyama et al. |
| 2012/0211367 A1 | 8/2012 | Vecitis |
| 2012/0218508 A1 | 8/2012 | Pugh et al. |
| 2012/0219203 A1 | 8/2012 | Adachi |
| 2012/0220053 A1 | 8/2012 | Lee et al. |
| 2012/0234453 A1 | 9/2012 | Pugh et al. |
| 2012/0234679 A1 | 9/2012 | Garaj et al. |

(56) References Cited

U.S. PATENT DOCUMENTS

| | | |
|---|---|---|
| 2012/0235277 A1 | 9/2012 | Pugh et al. |
| 2012/0236254 A1 | 9/2012 | Pugh et al. |
| 2012/0236524 A1 | 9/2012 | Pugh et al. |
| 2012/0241371 A1 | 9/2012 | Revanur et al. |
| 2012/0242953 A1 | 9/2012 | Pugh et al. |
| 2012/0255899 A1 | 10/2012 | Choi et al. |
| 2012/0267337 A1 | 10/2012 | Striemer et al. |
| 2012/0292245 A1 | 11/2012 | Saito |
| 2012/0294793 A1 | 11/2012 | Chen et al. |
| 2012/0298396 A1 | 11/2012 | Hong et al. |
| 2012/0301707 A1 | 11/2012 | Kinloch et al. |
| 2013/0015136 A1 | 1/2013 | Bennett |
| 2013/0034760 A1 | 2/2013 | Otts et al. |
| 2013/0045523 A1 | 2/2013 | Leach et al. |
| 2013/0056367 A1 | 3/2013 | Martinez et al. |
| 2013/0071941 A1 | 3/2013 | Miller |
| 2013/0096292 A1 | 4/2013 | Brahmasandra et al. |
| 2013/0100436 A1 | 4/2013 | Jackson et al. |
| 2013/0105417 A1 | 5/2013 | Stetson et al. |
| 2013/0108839 A1 | 5/2013 | Arnold et al. |
| 2013/0116541 A1 | 5/2013 | Gracias et al. |
| 2013/0131214 A1 | 5/2013 | Scales et al. |
| 2013/0135578 A1 | 5/2013 | Pugh et al. |
| 2013/0146221 A1 | 6/2013 | Kolmakov et al. |
| 2013/0146480 A1 | 6/2013 | Garaj et al. |
| 2013/0152386 A1 | 6/2013 | Pandojirao-S et al. |
| 2013/0174968 A1 | 7/2013 | Vlassiouk et al. |
| 2013/0174978 A1 | 7/2013 | Pugh et al. |
| 2013/0176030 A1 | 7/2013 | Simon |
| 2013/0190476 A1 | 7/2013 | Lancaster et al. |
| 2013/0192460 A1 | 8/2013 | Miller et al. |
| 2013/0192461 A1 | 8/2013 | Miller et al. |
| 2013/0194540 A1 | 8/2013 | Pugh et al. |
| 2013/0213568 A1 | 8/2013 | Pugh et al. |
| 2013/0215377 A1 | 8/2013 | Pugh et al. |
| 2013/0215378 A1 | 8/2013 | Pugh et al. |
| 2013/0215380 A1 | 8/2013 | Pugh et al. |
| 2013/0216581 A1 | 8/2013 | Fahmy et al. |
| 2013/0240355 A1 | 9/2013 | Ho et al. |
| 2013/0240437 A1 | 9/2013 | Rodrigues et al. |
| 2013/0248097 A1 | 9/2013 | Ploss, Jr. |
| 2013/0248367 A1 | 9/2013 | Stetson et al. |
| 2013/0249147 A1 | 9/2013 | Bedworth |
| 2013/0256118 A1 | 10/2013 | Meller et al. |
| 2013/0256139 A1 | 10/2013 | Peng |
| 2013/0256154 A1 | 10/2013 | Peng |
| 2013/0256210 A1 | 10/2013 | Fleming |
| 2013/0256211 A1 | 10/2013 | Fleming |
| 2013/0261568 A1 | 10/2013 | Martinson et al. |
| 2013/0269819 A1 | 10/2013 | Ruby et al. |
| 2013/0270188 A1 | 10/2013 | Karnik et al. |
| 2013/0273288 A1 | 10/2013 | Luo et al. |
| 2013/0277305 A1 | 10/2013 | Stetson et al. |
| 2013/0277573 A1 | 10/2013 | Miller et al. |
| 2013/0284665 A1 | 10/2013 | Lee et al. |
| 2013/0295150 A1 | 11/2013 | Chantalat et al. |
| 2013/0295374 A1 | 11/2013 | Tang et al. |
| 2013/0309776 A1 | 11/2013 | Drndic et al. |
| 2013/0317131 A1 | 11/2013 | Scales et al. |
| 2013/0317132 A1 | 11/2013 | Scales et al. |
| 2013/0317133 A1 | 11/2013 | Scales et al. |
| 2013/0323295 A1 | 12/2013 | Scales et al. |
| 2013/0330833 A1 | 12/2013 | Ruiz et al. |
| 2013/0335092 A1 | 12/2013 | Wu |
| 2013/0338611 A1 | 12/2013 | Pugh et al. |
| 2013/0338744 A1 | 12/2013 | Frewin et al. |
| 2014/0002788 A1 | 1/2014 | Otts et al. |
| 2014/0005514 A1 | 1/2014 | Pugh et al. |
| 2014/0015160 A1 | 1/2014 | Kung et al. |
| 2014/0017322 A1 | 1/2014 | Dai et al. |
| 2014/0021133 A1 | 1/2014 | Siwy et al. |
| 2014/0030482 A1 | 1/2014 | Miller et al. |
| 2014/0048411 A1 | 2/2014 | Choi et al. |
| 2014/0066958 A1 | 3/2014 | Priewe |
| 2014/0079936 A1 | 3/2014 | Russo et al. |
| 2014/0093728 A1 | 4/2014 | Shah et al. |
| 2014/0128891 A1 | 5/2014 | Astani-Matthies et al. |
| 2014/0141521 A1 | 5/2014 | Peng et al. |
| 2014/0151288 A1 | 6/2014 | Miller et al. |
| 2014/0151631 A1 | 6/2014 | Duesberg et al. |
| 2014/0154464 A1 | 6/2014 | Miller et al. |
| 2014/0170195 A1 | 6/2014 | Fassih et al. |
| 2014/0171541 A1 | 6/2014 | Scales et al. |
| 2014/0174927 A1 | 6/2014 | Bashir et al. |
| 2014/0190004 A1 | 7/2014 | Riall et al. |
| 2014/0190550 A1 | 7/2014 | Loh et al. |
| 2014/0190676 A1 | 7/2014 | Zhamu et al. |
| 2014/0190833 A1 | 7/2014 | Lieber et al. |
| 2014/0192313 A1 | 7/2014 | Riall et al. |
| 2014/0192314 A1 | 7/2014 | Riall et al. |
| 2014/0199777 A2 | 7/2014 | Ruiz et al. |
| 2014/0209539 A1 | 7/2014 | El Badawi et al. |
| 2014/0212596 A1 | 7/2014 | Jahangiri-Famenini |
| 2014/0230653 A1 | 8/2014 | Yu et al. |
| 2014/0230733 A1 | 8/2014 | Miller |
| 2014/0231351 A1 | 8/2014 | Wickramasinghe et al. |
| 2014/0248621 A1 | 9/2014 | Collins |
| 2014/0253131 A1 | 9/2014 | Liu et al. |
| 2014/0257348 A1 | 9/2014 | Priewe et al. |
| 2014/0257515 A1 | 9/2014 | So et al. |
| 2014/0257517 A1 | 9/2014 | Deichmann et al. |
| 2014/0259657 A1 | 9/2014 | Riall et al. |
| 2014/0261999 A1 | 9/2014 | Stetson et al. |
| 2014/0263035 A1 | 9/2014 | Stoltenberg et al. |
| 2014/0263178 A1 | 9/2014 | Sinton et al. |
| 2014/0264977 A1 | 9/2014 | Pugh et al. |
| 2014/0268015 A1 | 9/2014 | Riall et al. |
| 2014/0268020 A1 | 9/2014 | Pugh et al. |
| 2014/0268021 A1 | 9/2014 | Pugh et al. |
| 2014/0268026 A1 | 9/2014 | Pugh et al. |
| 2014/0272286 A1 | 9/2014 | Stoltenberg et al. |
| 2014/0272522 A1 | 9/2014 | Pugh et al. |
| 2014/0273315 A1 | 9/2014 | Pugh et al. |
| 2014/0273316 A1 | 9/2014 | Pugh et al. |
| 2014/0276481 A1 | 9/2014 | Pugh et al. |
| 2014/0276999 A1 | 9/2014 | Harms et al. |
| 2014/0306361 A1 | 10/2014 | Pugh et al. |
| 2014/0308681 A1 | 10/2014 | Strano et al. |
| 2014/0311967 A1 | 10/2014 | Grossman et al. |
| 2014/0315213 A1 | 10/2014 | Nagrath et al. |
| 2014/0318373 A1 | 10/2014 | Wood et al. |
| 2014/0322518 A1 | 10/2014 | Addleman et al. |
| 2014/0333892 A1 | 11/2014 | Pugh et al. |
| 2014/0335661 A1 | 11/2014 | Pugh et al. |
| 2014/0343580 A1 | 11/2014 | Priewe |
| 2014/0346081 A1 | 11/2014 | Sowden et al. |
| 2014/0346631 A1 | 11/2014 | Karim et al. |
| 2014/0349892 A1 | 11/2014 | Van Der Zaag et al. |
| 2014/0350372 A1 | 11/2014 | Pugh et al. |
| 2014/0377651 A1 | 12/2014 | Kwon et al. |
| 2014/0377738 A1 | 12/2014 | Bachmann et al. |
| 2015/0015843 A1 | 1/2015 | Pugh et al. |
| 2015/0017918 A1 | 1/2015 | Pugh et al. |
| 2015/0050734 A1 | 2/2015 | Liedtke et al. |
| 2015/0053627 A1 | 2/2015 | Silin et al. |
| 2015/0057762 A1 | 2/2015 | Harms et al. |
| 2015/0061990 A1 | 3/2015 | Toner et al. |
| 2015/0062533 A1 | 3/2015 | Toner et al. |
| 2015/0063605 A1 | 3/2015 | Pugh |
| 2015/0066063 A1 | 3/2015 | Priewe |
| 2015/0075667 A1 | 3/2015 | McHugh et al. |
| 2015/0076056 A1 | 3/2015 | Iyuke et al. |
| 2015/0077658 A1 | 3/2015 | Pugh et al. |
| 2015/0077659 A1 | 3/2015 | Pugh et al. |
| 2015/0077660 A1 | 3/2015 | Pugh et al. |
| 2015/0077661 A1 | 3/2015 | Pugh et al. |
| 2015/0077662 A1 | 3/2015 | Pugh et al. |
| 2015/0077663 A1 | 3/2015 | Pugh et al. |
| 2015/0077699 A1 | 3/2015 | De Sio et al. |
| 2015/0077702 A9 | 3/2015 | Pugh et al. |
| 2015/0079683 A1 | 3/2015 | Yager et al. |
| 2015/0087249 A1 | 3/2015 | Pugh et al. |
| 2015/0096935 A1 | 4/2015 | Mitra et al. |
| 2015/0098910 A1 | 4/2015 | Mordas et al. |

(56) References Cited

U.S. PATENT DOCUMENTS

| | | |
|---|---|---|
| 2015/0101931 A1 | 4/2015 | Garaj et al. |
| 2015/0105686 A1 | 4/2015 | Vasan |
| 2015/0118318 A1 | 4/2015 | Fahmy et al. |
| 2015/0122727 A1 | 5/2015 | Karnik et al. |
| 2015/0137817 A1 | 5/2015 | Wilson et al. |
| 2015/0138454 A1 | 5/2015 | Pugh et al. |
| 2015/0142107 A1 | 5/2015 | Pugh et al. |
| 2015/0145155 A1 | 5/2015 | Pugh et al. |
| 2015/0146162 A1 | 5/2015 | Pugh et al. |
| 2015/0147474 A1 | 5/2015 | Batchvarova et al. |
| 2015/0151254 A1 | 6/2015 | Perez |
| 2015/0170788 A1 | 6/2015 | Miller et al. |
| 2015/0174253 A1 | 6/2015 | Sun et al. |
| 2015/0174254 A1 | 6/2015 | Sun et al. |
| 2015/0182473 A1 | 7/2015 | Bosnyak et al. |
| 2015/0185180 A1 | 7/2015 | Ruhl et al. |
| 2015/0196579 A1 | 7/2015 | Ferrante et al. |
| 2015/0196879 A1 | 7/2015 | Brinke-Seiferth et al. |
| 2015/0202351 A1 | 7/2015 | Kaplan et al. |
| 2015/0212339 A1 | 7/2015 | Pugh et al. |
| 2015/0217219 A1 | 8/2015 | Sinsabaugh et al. |
| 2015/0218210 A1 | 8/2015 | Stetson et al. |
| 2015/0221474 A1 | 8/2015 | Bedworth |
| 2015/0231557 A1 | 8/2015 | Miller et al. |
| 2015/0231577 A1 | 8/2015 | Nair et al. |
| 2015/0247178 A1 | 9/2015 | Mountcastle et al. |
| 2015/0248972 A1 | 9/2015 | Tang et al. |
| 2015/0258254 A1 | 9/2015 | Simon et al. |
| 2015/0258498 A1 | 9/2015 | Simon et al. |
| 2015/0258502 A1 | 9/2015 | Turowski |
| 2015/0258503 A1 | 9/2015 | Sinton et al. |
| 2015/0258506 A1 | 9/2015 | Mi et al. |
| 2015/0258525 A1 | 9/2015 | Westman et al. |
| 2015/0268150 A1 | 9/2015 | Newkirk et al. |
| 2015/0272896 A1 | 10/2015 | Sun et al. |
| 2015/0273401 A1 | 10/2015 | Miller et al. |
| 2015/0309337 A1 | 10/2015 | Flitsch et al. |
| 2015/0321147 A1 | 11/2015 | Fleming et al. |
| 2015/0321149 A1 | 11/2015 | McGinnis |
| 2015/0323811 A1 | 11/2015 | Flitsch et al. |
| 2015/0336202 A1 | 11/2015 | Bedworth et al. |
| 2015/0342900 A1 | 12/2015 | Putnins |
| 2015/0346382 A1 | 12/2015 | Bliven et al. |
| 2015/0351887 A1 | 12/2015 | Peters |
| 2015/0359742 A1 | 12/2015 | Fassih et al. |
| 2015/0376448 A1 | 12/2015 | Urs |
| 2015/0378176 A1 | 12/2015 | Flitsch et al. |
| 2016/0009049 A1 | 1/2016 | Stoltenberg et al. |
| 2016/0038885 A1 | 2/2016 | Hogen-Esch et al. |
| 2016/0043384 A1 | 2/2016 | Zhamu et al. |
| 2016/0058932 A1 | 3/2016 | Stetson et al. |
| 2016/0059190 A1 | 3/2016 | Yoo et al. |
| 2016/0067390 A1 | 3/2016 | Simon et al. |
| 2016/0074814 A1 | 3/2016 | Park et al. |
| 2016/0074815 A1 | 3/2016 | Sinton et al. |
| 2016/0084008 A1 | 3/2016 | Faircloth et al. |
| 2016/0084981 A1 | 3/2016 | Kayano et al. |
| 2016/0116237 A1 | 4/2016 | Alsadah et al. |
| 2016/0256805 A1 | 9/2016 | Grein et al. |
| 2016/0272499 A1 | 9/2016 | Graphenea |
| 2016/0282326 A1 | 9/2016 | Waduge et al. |
| 2016/0284811 A1 | 9/2016 | Yu et al. |
| 2016/0339160 A1 | 11/2016 | Bedworth et al. |
| 2017/0000937 A1 | 1/2017 | Gottschalk |
| 2017/0028640 A1 | 2/2017 | Harrison et al. |
| 2017/0032962 A1 | 2/2017 | Graphenea |
| 2017/0035943 A1 | 2/2017 | Simon et al. |
| 2017/0036916 A1 | 2/2017 | Bedworth et al. |
| 2017/0037356 A1 | 2/2017 | Simon et al. |
| 2017/0057812 A1 | 3/2017 | Graphenea |
| 2017/0065939 A1 | 3/2017 | Kim et al. |
| 2017/0144107 A1 | 5/2017 | Garaj et al. |
| 2017/0202885 A1 | 7/2017 | Agulnick |
| 2017/0216923 A1 | 8/2017 | Babenko et al. |
| 2017/0217777 A1 | 8/2017 | Hong et al. |
| 2017/0239623 A1 | 8/2017 | Stoltenberg et al. |
| 2017/0296706 A1 | 10/2017 | Simon et al. |
| 2017/0296972 A1 | 10/2017 | Sinton et al. |
| 2017/0296976 A1 | 10/2017 | Liu et al. |
| 2017/0296979 A1 | 10/2017 | Swett et al. |
| 2018/0147542 A1 | 5/2018 | Jhon et al. |
| 2018/0207591 A1 | 7/2018 | Yu et al. |

FOREIGN PATENT DOCUMENTS

| | | |
|---|---|---|
| CN | 1128501 A | 8/1996 |
| CN | 101108194 A | 1/2008 |
| CN | 101243544 | 8/2008 |
| CN | 101428198 A | 5/2009 |
| CN | 101489653 A | 7/2009 |
| CN | 101996853 A | 3/2011 |
| CN | 102242062 A | 11/2011 |
| CN | 102344132 | 2/2012 |
| CN | 102423272 | 4/2012 |
| CN | 102592720 A | 7/2012 |
| CN | 101996853 B | 8/2012 |
| CN | 102637584 A | 8/2012 |
| CN | 103153441 | 6/2013 |
| CN | 103182249 A | 7/2013 |
| CN | 203235358 | 10/2013 |
| CN | 103480281 | 1/2014 |
| CN | 103585891 | 2/2014 |
| CN | 103603706 A | 2/2014 |
| DE | 19536560 | 3/1997 |
| DE | 10 2005 049 388 A1 | 4/2007 |
| EP | 0 364 628 A1 | 4/1990 |
| EP | 1 034 251 | 1/2004 |
| EP | 1 777 250 A1 | 4/2007 |
| EP | 1 872 812 | 1/2008 |
| EP | 2 060 286 | 5/2009 |
| EP | 2 107 120 A1 | 10/2009 |
| EP | 2 230 511 A1 | 9/2010 |
| EP | 1 603 609 | 5/2011 |
| EP | 2 354 272 | 8/2011 |
| EP | 2 450 096 | 5/2012 |
| EP | 2 489 520 | 8/2012 |
| EP | 2 511 002 | 10/2012 |
| EP | 2 586 473 | 5/2013 |
| EP | 2 679 540 | 1/2014 |
| EP | 2 937 313 | 10/2015 |
| EP | 2 995 368 A1 | 3/2016 |
| EP | 3 070 053 | 9/2016 |
| EP | 3 084 398 | 10/2016 |
| EP | 1 538 2430.5 | 3/2017 |
| EP | 3 135 631 | 3/2017 |
| JP | 59-102111 | 7/1984 |
| JP | 10-510471 | 5/1995 |
| JP | 7504120 | 5/1995 |
| JP | H09-232293 A | 9/1997 |
| JP | 2001-232158 | 8/2001 |
| JP | 2002-126510 | 5/2002 |
| JP | 2004-179014 | 6/2004 |
| JP | 2005-126966 | 5/2005 |
| JP | 2006-188393 | 7/2006 |
| JP | 2006-262891 A | 10/2006 |
| JP | 2009-291777 | 12/2009 |
| JP | 2011-168448 A | 9/2011 |
| JP | 2011-241479 | 12/2011 |
| JP | 2012-500708 | 1/2012 |
| JP | 2013-536077 A | 9/2013 |
| JP | 2004-202480 | 7/2014 |
| JP | 2015-503405 | 2/2015 |
| JP | 2016-175828 | 10/2016 |
| KR | 1020110084110 | 7/2011 |
| KR | 10-2012-0022164 A | 3/2012 |
| KR | 1020120022164 A1 | 3/2012 |
| KR | 1020140002570 | 1/2014 |
| WO | WO-93/33901 | 3/1993 |
| WO | WO-93/12859 | 8/1993 |
| WO | WO-95/00231 | 1/1995 |
| WO | WO-97/12664 A1 | 4/1997 |
| WO | WO-98/30501 A2 | 7/1998 |
| WO | WO-00/70012 | 11/2000 |
| WO | WO-02/055539 A1 | 7/2002 |

(56) References Cited

FOREIGN PATENT DOCUMENTS

| WO | WO-2013/115762 | | 8/2003 |
|---|---|---|---|
| WO | WO-2004/009840 | A1 | 1/2004 |
| WO | WO-2004/082733 | | 9/2004 |
| WO | WO-2005/047857 | A2 | 5/2005 |
| WO | WO-2007/103411 | A2 | 9/2007 |
| WO | WO-2007/140252 | A1 | 12/2007 |
| WO | WO-2008/008533 | | 1/2008 |
| WO | WO-2009/129984 | A1 | 10/2009 |
| WO | WO-2010/006080 | | 1/2010 |
| WO | WO-2010/115904 | A1 | 10/2010 |
| WO | WO-2011/019686 | A1 | 2/2011 |
| WO | WO-2011/046706 | A1 | 4/2011 |
| WO | WO-2011/001674 | | 6/2011 |
| WO | WO-2011/063458 | A1 | 6/2011 |
| WO | WO-2011/075158 | | 6/2011 |
| WO | WO-2011/094204 | A2 | 8/2011 |
| WO | WO-2011/100458 | A2 | 8/2011 |
| WO | WO-2011/138689 | A2 | 11/2011 |
| WO | WO-2012/006657 | A1 | 1/2012 |
| WO | WO-2012/021801 | A2 | 2/2012 |
| WO | WO-2012/027148 | A1 | 3/2012 |
| WO | WO-2012/028695 | | 3/2012 |
| WO | WO-2012/030368 | A1 | 3/2012 |
| WO | WO-2012/073998 | A1 | 6/2012 |
| WO | WO-2012/125770 | | 9/2012 |
| WO | WO-2012/138671 | A2 | 10/2012 |
| WO | WO-2012/142852 | A1 | 10/2012 |
| WO | WO-2013/016445 | A1 | 1/2013 |
| WO | WO-2013/048063 | A1 | 4/2013 |
| WO | WO-2013/138137 | A1 | 9/2013 |
| WO | WO-2013/138698 | A1 | 9/2013 |
| WO | WO-2013/142133 | | 9/2013 |
| WO | WO-2013/142539 | | 9/2013 |
| WO | WO-2013/151799 | | 10/2013 |
| WO | WO-2013/152179 | A1 | 10/2013 |
| WO | WO-2014/038600 | A1 | 3/2014 |
| WO | WO-2014/084856 | | 6/2014 |
| WO | WO-2014/084861 | A1 | 6/2014 |
| WO | WO-2014/159043 | | 10/2014 |
| WO | WO-2014/168629 | A1 | 10/2014 |
| WO | WO-2014/204722 | A1 | 12/2014 |
| WO | WO-2015/030698 | A1 | 3/2015 |
| WO | WO-2015/110277 | | 7/2015 |
| WO | WO-2015/116857 | | 8/2015 |
| WO | WO-2015/116946 | | 8/2015 |
| WO | WO-2015/138736 | A1 | 9/2015 |
| WO | WO-2015/138752 | A1 | 9/2015 |
| WO | WO-2015/1138771 | A1 | 9/2015 |
| WO | WO-2015/197217 | | 12/2015 |
| WO | WO-2016/036888 | A1 | 3/2016 |
| WO | WO-2016/102003 | | 6/2016 |

OTHER PUBLICATIONS

AE Search and Examination Report for United Arab Emirates Application No. P186/13 dated Oct. 4, 2016.
Allen et al., "Craters on silicon surfaces created by gas cluster ion impacts," Journal of Applied Physics, 92(7): 3671-3678 (Oct. 1, 2002).
Aluru et al. "Modeling electronics on the nanoscale." Handbook of nanoscience, engineering and technology Goddard W, Brenner D, Lyshevski S, Iafrate GJ (2002): 11-1.
Alvarenga, "Carbon nanotube materials for aerospace wiring" Rochester Institute of Technology, 2010.
AMI Applied Membranes Inc. (undated). FilmTec Nanofiltration Membrane Elements. Retrieved Jun. 1, 2016, from http://www.appliedmembranes.com/filmtec-nanofiltration-membrane-elements.html.
AMI Applied Membranes Inc., "Filmtec Nanofiltration Membrane Elements", Retrieved from appliedmembranes.com/nanofiltration_elements.htm, accessed Apr. 28, 2015 (2 Pages).
Apel, P. "Track etching technique in membrane technology." Radiation Measurements 34.1 (2001): 559-566.
Atmeh et al., "Albumin Aggregates: Hydrodynamic Shape and Physico-Chemical Properties," Jordan Journal of Chemistry, 2(2): 169-182 (Accepted Jul. 29, 2007).
AU Examination Report for Australian Patent Application No. 2013235234, dated Jan. 13, 2017, 4 pages.
AU Notice of Acceptance for Australian Application No. 2011293742 dated Jan. 13, 2016.
Bai et al., "Graphene nanomesh," Nature Nanotechnology 5: 190-194 (Feb. 14, 2010).
Baker, "Membrane Technology and Applications", Membrane Technology and Applications; Apr. 14, 2004; pp. 92-94.
Baker, "Track-etch Membranes," Membrane Technology and Applications 2: 92-9 (published online Dec. 2004).
Barreiro et al. "Transport properties of graphene in the high-current limit." Physical review letters 103.7 (2009): 076601.
Barreiro et al. "Understanding the catalyst-free transformation of amorphous carbon into graphene by current-induced annealing," Scientific Reports, 3 (Article 1115): 1-6 (Jan. 23, 2013).
Bieri et al. "Two-dimensional Polymer Formation on Surfaces: Insight into the Roles of Precursor Mobility and Reactivity" JACS, 2010, vol. 132, pp. 16669-16676.
Botari et al., "Graphene healing mechanisms: A theoretical investigation," Carbon, 99: 302-309 (Apr. 2016) (published online Dec. 12, 2015).
Bruin et al., "Maturation and function of human embryonic stem cell-derived pancreatic progenitors in macroencapsulation devices following transplant into mice", Diabetologia (2013), vol. 56: 1987-1998 (Jun. 16, 2013).
Butler et al. "Progress, Challenges, and Opportunities in Two-Dimensional Materials Beyond Graphene", Materials Review 7(4): 2898-2926 (Mar. 6, 2013).
Chen et al., "Defect Scattering in Graphene," Physical Review Letters, 102: 236805-1-236805-4 (Jun. 12, 2009).
Chen et al., "Mechanically Strong, Electrically Conductive, and Biocompatible Graphene Paper," Adv. Mater., 20(18): 3557-3561 (Sep. 2008) (available online Jul. 23, 2008).
Chen et al., "Self-healing of defected graphene," Applied Physics Letters, 102(10): 103107-1-103107-5 (Mar. 13, 2013).
Cheng et al., "Ion Transport in Complex Layered Graphene-Based Membranes with Tuneable Interlayer Spacing," Science Advances 2(2): 1501272 (Feb. 12, 2016).
Chhowalla et al., "The chemistry of two-dimensional layered transition metal dichalcogenide nanosheets," Nature Chemistry 5: 263-275 (Mar. 20, 2013).
Childres et al., "Effect of oxygen plasma etching on graphene studied using Raman spectroscopy and electronic transport measurements," New Journal of Physics 13, 1-12 (Feb. 10, 2011).
Chu Ju, et al. "Modern Biotechnology" East China University of Technology Press, (Sep. 2007), vol. 1; pp. 306-307, ISBN 978-7-5628-2116-8.
Clochard, "Radiografted track-etched polymer membranes for research and application" [Scholarly project], In Laboratoire Des Solides Irradiés, (undated), Retrieved Jun. 2, 2016, from http://iramis.cea.fr/radiolyse/5juin2015/Clochard.pdf.
Clochard, "Track-Etched Polymer Membranes," Laboratory of Irradiated Solids, Ecole Polytechnique, retrieved from http://www.lsi.polytechnique.fr/home/research/physics-and-chemistry-of-nano-objects/trac . . . , Accessed Jul. 30, 2015 (2 pages).
CN Office Action for Chinese Application No. 201380014845.X dated Jul. 8, 2016.
CN Office Action for Chinese Application No. 201380014845.X dated Sep. 2, 2015.
CN Office Action for Chinese Application No. 201380019165.5 dated Aug. 25, 2015.
CN Office Action for Chinese Application No. 201380073141.X dated Jun. 8, 2016.
CN Office Action for Chinese Application No. 201380073141.X dated Mar. 21, 2017.
CN Office Action for Chinese Application No. 201480015372.X dated Aug. 2, 2016.
CN Office Action for Chinese Application No. 20118004918.5 dated Jun. 15, 2015.

(56) References Cited

OTHER PUBLICATIONS

CN Office Action for Chinese Application No. 201180049184.5 dated Jul. 30, 2014.
CN Office Action for Chinese Application No. 201180049184.5 dated Mar. 4, 2016.
CN Office Action for Chinese Application No. 201380014845.X dated Dec. 23, 2016.
CN Office Action for Chinese Application No. 201380017644.5 dated Feb. 7, 2017.
CN Office Action for Chinese Application No. 201380017644.5 dated May 26, 2016.
CN Office Action for Chinese Application No. 201380017644.5 dated Sep. 29, 2015.
CN Office Action in Chinese Application No. 201380013988.9 dated Aug. 18, 2016 (English translation not readily available).
CN Office Action in Chinese Application No. 201380013988.9 dated Oct. 27, 2015.
Cohen-Tanugi, "Nanoporous graphene as a water desalination membrane," (Ph.D. Thesis, Massachusetts Institute of Technology) (Jun. 2015).
Colton, "Implantable biohybrid artificial organs," Cell Transplantation 4(4): 415-436 (Mar. 28, 1995).
Crock et al., "Polymer Nanocomposites with Graphene-Based Hierarchical Fillers as Materials for Multifunctional Water Treatment Membranes." Water Research 47(12): 3984-3996 (Aug. 2013; first published online Mar. 29, 2013).
Daniel et al. "Implantable Diagnostic Device for Cancer Monitoring." Biosens Bioelectricon. 24(11): 3252-3257 (Jul. 15, 2009).
Database WPI, Week 201238, Thomson Scientific, London, GB; AN 2012-D49442.
De Lannoy et al., "Aquatic Biofouling Prevention by Electrically Charged Nanocomposite Polymer Thin Film Membranes", 2013 American Water Work Association membrane Technology Conference; Environmental science & technology 47.6 (2013): 2760-2768.
Desai et al., "Nanoporous microsystems for islet cell replacement," Advanced Drug Delivery Reviews 56: 1661-1673 (Jul. 23, 2004).
Dong et al., "Growth of large-sized graphene thin-films by liquid precursor-based chemical vapor deposition under atmospheric pressure," Carbon 49(11): 3672-3678 (May 7, 2011).
Edwards, "Large Sheets of Graphene Film Produced for Transparent Electrodes (w/ Video)", (Jun. 21, 2010), PhysOrg.com, retrieved on May 15, 2017 from https://phys.org/news/2010-06-large-sheets-graphene-transparentelectrodes.html (2 pages).
EP Office Action for European Application No. 13715529.7 dated Jun. 24, 2016.
Fayerman, "Canadian scientists use stem cells to reverse diabetes in mice", The Telegraph-Journal (New Brunswick), 1-2 (Jun. 29, 2012).
Fayerman, "Diabetes reversed in mice; University of B.C. scientists use embryonic stem cells to deal with Type 1 disease", The Vancouver Sun (British Columbia), 1-2 (Jun. 28, 2012).
Fejes et al. "A review of the properties and CVD synthesis of coiled carbon nanotubes." Materials 3.4 (2010): 2618-2642.
Fischbein et al., "Electron beam nanosculpting of suspended graphene sheets," Applied Physics Letters 93(113107): 1-3, (Sep. 16, 2008).
Fissell et al., "High-Performance Silicon Nanopore Hemofiltration Membranes," NIH-PA Author Manuscript, PMC, (Jan. 5, 2010), also published in J. Memb. Sci. 326(1): 1-15 (Jan. 5, 2009).
Franzen, C. "MIT Setting Up Industrial-Scale Graphene Printing Press" Sep. 23, 2011, retrieved from http://talkingpointsmemo.com/idealab/mit-setting-up-industrial-scale-graphene-printing-press (2 pages).
Fuertes, "Carbon composite membranes from Matrimid® and Kapton® polyimides for gas separation," Microporous and Mesoporous Materials, 33: 115-125 (Jun. 16, 1999).
Galashev, "Computer study of the removal of Cu from the graphene surface using Ar clusters," Computational Materials Science, 98: 123-128 (Feb. 2015) (available online Nov. 3, 2014).
Georgakilas et al., "Functionalization of Graphene: Covalent and Non-Covalent Approaches, Derivatives and Applications," Chem. Rev., (2012) 112(11), pp. 6156-6214.

Gimi et al., "A Nanoporous, Transparent Microcontainer for Encapsulated Islet Therapy," J. Diabetes Sci. Tech. 3(2): 1-7 (Mar. 2009).
Han et al., "Ultrathin Graphene Nanofiltration Membrane for Water Purification." Advanced Functional Materials 23(29): 3693-3700 (Aug. 1, 2013).
Harvey "Carbon as conductor: a pragmatic view." Proceedings of the 61st IWCS Conference, http://www.iwcs.org/archives/56333-iwcs-2012b-1.1584632. vol. 1. 2012.
Hashimoto et al. "Direct evidence for atomic defects in graphene layers." Nature 430.7002 (2004): 870-873.
He, et al. "The attachment of Fe3 O4 nanoparticles to graphene oxide by covalent bonding." Carbon 48.11 (2010): 3139-3144.
Hone et al. "Graphene has record-breaking strength" Physicsworld.com, Jul. 17, 2008.
Hong et al., "Graphene multilayers as gates for multi-week sequential release of proteins from surfaces," NIH-PA Author Manuscript PMC (Jun. 1, 2014), also published in ACS Nano, 6(1): 81-88 (Jan. 24, 2012) (available online Dec. 2011).
Hu et al., "Enabling graphene oxide nanosheets as water separation membranes," Environmental Science & Technology 47(8): 3715-3723 (Mar. 14, 2013).
Humplik, et al. "Nanostructured materials for water desalination." Nanotechnology 22.29 (2011): 292001.
International Search Report and Written Opinion in PCT/US2015/028948 dated Jul. 16, 2015.
International Search Report and Written Opinion dated Dec. 20, 2016 from related PCT application PCT/US2016/052010.
International Search Report and Written Opinion dated Jan. 13, 2017 from related PCT application PCT/US2016/027583.
International Search Report and Written Opinion dated Jan. 13, 2017 from related PCT application PCT/US2016/027594.
International Search Report and Written Opinion dated Jan. 13, 2017 from related PCT application PCT/US2016/027631.
International Search Report and Written Opinion dated Jan. 5, 2012 for related International Application No. PCT/US11/47800.
International Search Report and Written Opinion dated Jan. 6, 2017 from related PCT application PCT/US2016/027590.
International Search Report and Written Opinion dated Jan. 9, 2017 from related PCT application PCT/US2016/027628.
International Search Report and Written Opinion dated Mar. 12, 2014 for International Application No. PCT/US2013/074942.
International Search Report and Written Opinion for International Application No. PCT/US2011/047800 dated Jan. 5, 2012.
International Search Report and Written Opinion for PCT Application No. PCT/US2014/023027 dated Jun. 26, 2014.
International Search Report and Written Opinion in International Application No. PCT/US2013/030344 dated Jun. 19, 2013.
International Search Report and Written Opinion in International Application No. PCT/US2013/033035 dated Jun. 28, 2013.
International Search Report and Written Opinion in International Application No. PCT/US2013/033400, dated Jun. 28, 2013.
International Search Report and Written Opinion in International Application No. PCT/US2013/033403 dated Jun. 28, 2013.
International Search Report and Written Opinion in PCT/US2016/027632 dated Jan. 9, 2017.
International Search Report and Written Opinion dated Jun. 5, 2014 in International Application No. PCT/US2014/021677.
International Search Report and Written Opinion dated Jun. 6, 2014 in International Application No. PCT/US2014/023043.
International Search Report and Written Opinion dated Dec. 16, 2014, for International Application No. PCT/US2014/051011.
International Search Report and Written Opinion dated Jun. 19, 2015, in International Application No. PCT/US2015/020287.
International Search Report and Written Opinion of the International Searching Authority dated Apr. 30, 2015, from related PCT application PCT/US2015/013805.
International Search Report and Written Opinion of the International Searching Authority dated Jul. 20, 2015, from related PCT application PCT/US15/13599.
International Search Report and Written Opinion of the International Searching Authority dated Jul. 22, 2016, from related PCT application PCT/US2016/027596.

(56) References Cited

OTHER PUBLICATIONS

International Search Report and Written Opinion of the International Searching Authority dated Jul. 22, 2016, from related PCT application PCT/US2016/027603.
International Search Report and Written Opinion of the International Searching Authority dated Jul. 22, 2016, from related PCT application PCT/US2016/027607.
International Search Report and Written Opinion of the International Searching Authority dated Jul. 22, 2016, from related PCT application PCT/US2016/027610.
International Search Report and Written Opinion of the International Searching Authority dated Jul. 22, 2016, from related PCT application PCT/US2016/027612.
International Search Report and Written Opinion of the International Searching Authority dated Jul. 22, 2016, from related PCT application PCT/US2016/027616.
International Search Report and Written Opinion of the International Searching Authority dated Jun. 10, 2015, from related PCT application PCT/US2015/020246.
International Search Report and Written Opinion of the International Searching Authority dated Jun. 17, 2015, from related PCT application PCT/US2015/020296.
International Search Report and Written Opinion of the International Searching Authority dated Jun. 22, 2016, from related PCT application PCT/US2016/027637.
International Search Report and Written Opinion of the International Searching Authority dated Jun. 3, 2015, from related PCT application in PCT/US 2015/018114.
International Search Report and Written Opinion of the International Searching Authority dated Oct. 6, 2015, from related PCT application in PCT/US2015/029932.
International Search Report dated Dec. 27, 2016 from related PCT application PCT/US2016/052007.
International Search Report dated Dec. 4, 2015, in related PCT application PCT/US2015/048205.
International Search Report dated Jun. 10, 2015, from related PCT application PCT/US2015/020201.
International Search Report dated Dec. 8, 2016 from related PCT application PCT/US2016/027629.
International Search Report for PCT Application No. PCT/US2015/018114 dated Jun. 3, 2015.
Inui et al. "Molecular dynamics simulations of nanopore processing in a graphene sheet by using gas cluster ion beam." Applied Physics A: Materials Science & Processing 98.4 (2010): 787-794.
Inui et al., "Molecular dynamics simulations of nanopore processing in a graphene sheet by using gas cluster ion beam," Appl. Phys. A, 98: 787-794 (available online Dec. 19, 2009).
Israelachvili, "Intermolecular and Surface Forces," 3rd ed., Chap. 7.1, Sizes of Atoms, Molecules, and Ions, 2011, 1 page.
Joshi et al., "Precise and ultrafast molecular sieving through graphene oxide membranes", Science 343(6172): 752-754 (Feb. 14, 2014).
JP Office Action in Japanese Application No. 2015-501729 dated Dec. 9, 2016 (English translation).
JP Office Action in Japanese Application No. 2015-501867 dated Oct. 11, 2016 (English translation).
JP Office Action in Japanese Application No. 2015-503405 dated Nov. 14, 2016 (English translation).
JP Office Action in Japanese Application No. 2015-503406 dated Dec. 6, 2016(English translation).
Kanani et al., "Permeability—Selectivity Analysis for Ultrafiltration: Effect of Pore Geometry," NIH-PA Author Manuscript, PMC, (Mar. 1, 2011), also published in J. Memb. Sci. 349(1-2): 1-13(Mar. 1, 2010).
Kang et al., "Efficient Transfer of Large-Area Graphene Films onto Rigid Substrates by Hot Pressing," American Chemical Society Nano, 6(6): 5360-5365(May 28, 2012).
Khun et al. "From Microporous Regular Frameworks to Mesoporous Materials with Ultrahigh Surface Area: Dynamic reorganization of Porous Polymer Networks" JACS, 2008; vol. 130; pp. 13333-13337.
Kim et al., "The structural and electrical evolution of graphene by oxygen plasma-induced disorder," Nanotechnology IOP 20(375703): 1-8 (Aug. 26, 2009).
Kjeldsen, T., "Yeast secretory expression of insulin precursors," Appl Microbiol Biotechnol, 54: 277-286 (May 2, 2000).
Koh et al., "Sensitive NMR Sensors Detect Antibodies to Influenza," NIH PA Author Manuscript PMC (Apr. 13, 2009), also published in Angew. Chem. Int'l. Engl, 47(22): 4119-4121 (May 19, 2008) (available online Apr. 21, 2008).
Koski et al., "The New Skinny in Two-Dimensional Nanomaterials", ACS Nano 7(5): 3739-3743 (May 16, 2013).
Krupka et al., "Measurements of the Sheet Resistance And Conductivity Of Thin Epitaxial Graphene and SiC Films" Applied Physics Letters 96, 082101-I; Feb. 23, 2010.
Kurapati et al., "Graphene oxide based multilayer capsules with unique permeability properties: facile encapsulation of multiple drugs," Chemical Communications 48: 6013-6015 (Apr. 25, 2012).
Lathuiliere et al., "Encapsulated Cellular Implants for Recombinant Protein Delivery and Therapeutic Modulation of the Immune System," Journal of Applied Physics, Int. J. Mol. Sci., 16: 10578-10600 (May 8, 2015).
Lee, et al. "Measurement of the elastic properties and intrinsic strength of monolayer graphene." science 321.5887 (2008): 385-388.
Lehtinen et al., "Cutting and controlled modification of graphene with ion beams," Nanotechnology, 22: 175306 1-13 (Feb. 3, 2011).
Li et al., "3D graphene oxide-polymer hydrogel: near-infrared light-triggered active scaffold for reversible cell capture and on-demand release," Advanced Materials 25: 6737-6743 (Dec. 2014) (available online Oct. 7, 2013).
Lin et al., "A Direct and Polymer-Free Method for Transferring Graphene Grown By Chemical Vapor Deposition to Any Substrate," ACSNANO, 8(2): 1784-1791 (Jan. 28, 2014).
Liu et al. "Synthesis of high-quality monolayer and bilayer graphene on copper using chemical vapor deposition," Carbon, 49(13): 4122-4130 (Nov. 2011) (published online May 30, 2011).
Liu et al., "Atomically Thin Molybdenum Disulfide Nanopores with High Sensitivity for DNA Translocation," ACS Nano 8(3): 2504-2511 (Feb. 18, 2014).
Lucchese et al. "Quantifying ion-induced defects and Raman relaxation length in graphene." Carbon 48.5 (2010): 1592-1597.
MacLeod et al. "Supramolecular Orderinng in Oligothiophene-Fullerene Monolayers" JACS, 2009, vol. 131, pp. 16844-16850.
Marquardt et al., "Hybrid materials of platinum nanoparticles and thiol-functionalized graphene derivatives," Carbon 66: 285-294 (Jan. 2014) (available online Sep. 12, 2013).
Matteucci et al., "Transport of gases and Vapors in Glass and Rubbery Polymers," in Materials Science of Membranes for Gas and Vapor Separation. (Yampolskii et al., eds. 2006) (available online Jun. 2006).
Mattevi et al. "A review of chemical vapour deposition of graphene on copper." Journal of Materials Chemistry 21.10 (2011): 3324-3334.
Miao et al. "Chemical vapor deposition of grapheme" INTECH Open Access Publisher, 2011.
MIT/MTL Center for Graphene Devices and 2D Systems, retrieved from: http://www-mtl.mit.edu/wpmu/graphene/ [retrieved from Aug. 21, 2014 archive] (3 pages).
MIT/MTL Center for Graphene Devices and 2D Systems, retrieved from: http://www-mtl.mit.edu/wpmu/graphene/ [retrieved from Mar. 4, 2015 archive] (3 pages).
Morse, "Scalable Synthesis of Semiconducting Nanopatterned Graphene Materials," InterNano Resources for Nanomanufacturing; Apr. 30, 2010.
Nafea, et al. "Immunoisolating semi-permeable membranes for cell encapsulation: focus on hydrogels." J Control Release. 154(2): 110-122 (Sep. 5, 2011).
Nam et al., "Monodispersed PtCo nanoparticles on hexadecyltrimethylammonium bromide treated graphene as an effective oxygen reduction reaction catalyst for proton exchange membrane fuel cells," Carbon, 50: 3739-3747 (Aug. 2012) (available online Apr. 2012).

(56) References Cited

OTHER PUBLICATIONS

Nandamuri et al., "Chemical vapor deposition of graphene films," Nanotechnology 21(14): 145604 (4 pages) (Apr. 2010) (available online Mar. 10, 2010).
Nayini et al., "Synthesis and characterization of functionalized carbon nanotubes with different wetting behaviors and their influence on the wetting properties of carbon nanotubes/polymethylmethacrylate coatings," Progress in Organic Coatings 77(6): 1007-1014 (Feb. 25, 2014).
Notice of Allowance dated Oct. 7, 2016, from related U.S. Appl. No. 13/795,276.
O'Hern et al. "Selective Molecular Transport through Intrinsic Defects in a Single Layer of CVD Graphene," ACS Nano, 6(11): 10130-10138 (Oct. 2, 2012).
O'Hern et al., "Development of process to transfer large areas of LPCVD graphene from copper foil to a porous support substrate," 1-62 (M.S. Thesis, Massachusetts Institute of Technology, Thesis) (Sep. 2011).
O'Hern et al., "Nanofiltration across defect-sealed nanoporous monolayer graphene," Nano Letters, 15(5): 3254-3260 (published Apr. 27, 2015).
O'Hern et al., "Selective Ionic Transport through Tunable Subnanometer Pores in Single-Layer Graphene Membranes," Nano Letters 14(3): 1234-1241 (Feb. 3, 2014).
Ohgawara et al. "Assessment of pore size of semipermeable membrane for immunoisolation on xenoimplatntation of pancreatic B cells using a diffusion chamber." Transplant Proc. (6): 3319-3320. 1995.
Pall Corporation, "Pall Water Processing Disc-Tube Filter Technology", Retrieved on Feb. 10, 2015, Retrieved from http://www.pall.com /pdfs/Fuels-and-Chemicals/Disc-Tube_Filter_Technoloqy-DT100b.pdF (15 Pages).
Plant et al. "Size-dependent propagation of Au nanoclusters through few-layer grapheme," The Royal Society of Chemistry 2013, Nanoscale.
Plant et al. "Size-dependent propagation of Au nanoclusters through few-layer graphene," Nanoscale, 6: 1258-1263 (2014) (available online Oct. 27, 2013).
Pollard, "Growing Graphene via Chemical Vapor" Department of Physics, Pomona College; May 2, 2011.
Popok. "Cluster Ion Implantation in Graphite and Diamond: Radiation Damage and Stopping of Cluster Constituents," Reviews on Advanced Materials Science, 38(1): 7-16 (Jan. 21, 2014).
Rafael et al. "Cell Transplantation and Immunoisolation: Studies on a macroencapsultaion device." From the Departments of Transplantation Pathology: Stockholm, Sweden (1999).
Rezania et al., "Enrichment of Human Embryonic Stem Cell-Derived NKX6.1-Expressing Pancreatic Progenitor Cells Accelerates the Maturation of Insulin-Secreting Cells In Vivo", Stem Cells Regenerative Medicine, vol. 31: 2432-2442 (Jul. 29, 2013).
Rezania et al., "Maturation of Human Embryonic Stem Cell-Derived Pancreatic Progenitors Into Functional Islets Capable of Treating Pre-existing Diabetes in Mice", Diabetes Journal, vol. 61: 2016-2029 (Aug. 1, 2012).
Russo et al., "Atom-by-atom nucleation and growth of graphene nanopores," PNAS 109(16): 5953-5957 (Apr. 17, 2012).
SA Final Rejection for Saudi Arabia Application No. 113340400 dated Jan. 28, 2016.
SA First Examination Report for Saudi Arabia Application No. 113340401 dated Apr. 28, 2015.
SA First Examination Report for Saudi Arabia Application No. 113340424 dated May 10, 2015.
SA First Examination Report for Saudi Arabia Application No. 113340426 dated May 12, 2015.
SA First Examination Report in Saudi Arabia Application No. 113340400 dated Apr. 13, 2015.
SA Second Examination Report for Saudi Arabia Application No. 113340400 dated Aug. 11, 2015.
Sanchez, et al. "Biological Interactions of Graphene-Family Nanomaterials—An Interdisciplinary Review." Chem Res Toxicol. 25(1): 15-34 (Jan. 13, 2012).
Schweicher et al., "Membranes to achieve immunoprotection of transplanted islets," NIH-PA Author Manuscript, PMC, (Nov. 13, 2014), also published in Frontiers in Bioscience (Landmark Ed) 19: 49-76 (Jan. 1, 2014).
Sun et al., "Growth of graphene from solid carbon sources," Nature 468(7323): 549-552 (Nov. 25, 2010; including corrigendum in Nature 471(7336): 124 (Mar. 3, 2011).
Swett et al, "Supersonic Nanoparticle Interaction with Suspended CVD Graphene", Microsc. Microanal. 22 (Suppl 3): 1670-1671 (Jul. 25, 2016).
Tan et al., "Beta-cell regeneration and differentiation: how close are we to the 'holy grail'?" J. Mol. Encodrinol. 53(3): R119-R129 (Oct. 9, 2014).
Tang et al., "Highly wrinkled cross-linked graphene oxide membranes for biological and charge-storage applications," Small 8(3): 423-431 (Feb. 2012) (available online Dec. 13, 2011).
TW Office Action in Taiwanese Application No. 102146079 dated Apr. 14, 2017. 9 Pages.(English translation).
TW Search Report in Taiwanese Application No. 102146079 dated Apr. 14, 2017. 1 page.
UMEA Universitet "Graphene nanoscrolls are formed by decoration of magnetic nanoparticles." ScienceDaily. Aug. 15, 2013. https://www.sciencedaily.com/releases/2013/08/130815084402.htm (3 pages).
U.S. Notice of Allowance for U.S. Appl. No. 12/868,150 dated Sep. 25, 2012.
U.S. Notice of Allowance for U.S. Appl. No. 13/548,539 dated Aug. 18, 2015.
U.S. Notice of Allowance for U.S. Appl. No. 13/548,539 dated Jul. 23, 2015.
U.S. Notice of Allowance for U.S. Appl. No. 13/719,579 dated May 20, 2016.
U.S. Notice of Allowance for U.S. Appl. No. 13/795,276 dated Oct. 7, 2016.
U.S. Notice of Allowance for U.S. Appl. No. 13/802,896 dated Apr. 1, 2015.
U.S. Notice of Allowance for U.S. Appl. No. 13/803,958 dated Aug. 29, 2016.
U.S. Notice of Allowance for U.S. Appl. No. 13/803,958 dated Jun. 2, 2016.
U.S. Notice of Allowance for U.S. Appl. No. 13/803,958 dated Sep. 12, 2016.
U.S. Notice of Allowance for U.S. Appl. No. 13/804,085 dated Jan. 15, 2015.
U.S. Notice of Allowance for U.S. Appl. No. 13/804,085 dated Mar. 12, 2015.
U.S. Notice of Allowance for U.S. Appl. No. 14/200,195 dated Jul. 5, 2016.
U.S. Notice of Allowance for U.S. Appl. No. 14/200,530 dated Aug. 1, 2016.
U.S. Notice of Allowance for U.S. Appl. No. 14/203,655 dated Dec. 9, 2016.
U.S. Notice of Allowance in U.S. Appl. No. 12/868,150 dated Sep. 25, 2012.
U.S. Notice of Allowance in U.S. Appl. No. 13/795,276 dated Jan. 19, 2017.
U.S. Notice of Allowance in U.S. Appl. No. 13/803,958 dated Aug. 29, 2016.
U.S. Notice of Allowance in U.S. Appl. No. 13/803,958 dated Sep. 12, 2016.
U.S. Notice of Allowance in U.S. Appl. No. 14/610,770 dated May 5, 2017.
U.S. Notice of Allowance in U.S. Appl. No. 14/656,580 dated May 8, 2017.
U.S. Notice of Allowance in U.S. Appl. No. 14/819,273 dated Jun. 9, 2017.
U.S. Notice of Allowance in U.S. Appl. No. 15/099,464 dated Jun. 16, 2017.
U.S. Notice of Allowance in U.S. Appl. No. 13/480,569 dated Feb. 27, 2015.
U.S. Notice of Allowance in U.S. Appl. No. 14/610,770 dated Apr. 25, 2016.
U.S. Notice of Allowance in U.S. Appl. No. 14/610,770 dated Aug. 12, 2016.

(56) References Cited

OTHER PUBLICATIONS

U.S. Notice of Allowance in U.S. Appl. No. 14/610,770 dated Jan. 23, 2017.
U.S. Notice of Allowance in U.S. Appl. No. 14/819,273 dated Dec. 14, 2016.
U.S. Notice of Allowance in U.S. Appl. No. 14/819,273 dated Oct. 28, 2016.
U.S. Notice of Allowance in U.S. Appl. No. 14/856,198 dated Feb. 10, 2017.
U.S. Office Action for U.S. Appl. No. 13/548,539 dated Feb. 6, 2015.
U.S. Office Action for U.S. Appl. No. 13/719,579 dated Jul. 8, 2015.
U.S. Office Action for U.S. Appl. No. 13/719,579 dated May 4, 2016.
U.S. Office Action for U.S. Appl. No. 13/795,276 dated Apr. 22, 2016.
U.S. Office Action for U.S. Appl. No. 13/795,276 dated Oct. 6, 2015.
U.S. Office Action for U.S. Appl. No. 13/802,896 dated Sep. 24, 2014.
U.S. Office Action for U.S. Appl. No. 13/803,958 dated Aug. 11, 2014.
U.S. Office Action for U.S. Appl. No. 13/803,958 dated May 28, 2015.
U.S. Office Action for U.S. Appl. No. 13/803,958 dated Nov. 18, 2015.
U.S. Office Action for U.S. Appl. No. 14/031,300 dated Jan. 20, 2016.
U.S. Office Action for U.S. Appl. No. 14/031,300 dated Jul. 7, 2015.
U.S. Office Action for U.S. Appl. No. 14/200,195 dated Mar. 21, 2016.
U.S. Office Action for U.S. Appl. No. 14/200,195 dated Nov. 4, 2015.
U.S. Office Action for U.S. Appl. No. 14/200,530 dated Feb. 29, 2016.
U.S. Office Action for U.S. Appl. No. 14/203,655 dated Aug. 10, 2016.
U.S. Office Action for U.S. Appl. No. 14/656,190 dated May 18, 2017.
U.S. Office Action for U.S. Appl. No. 14/686,452 dated Jun. 9, 2017.
U.S. Office Action for U.S. Appl. No. 14/856,471 dated May 31, 2017.
U.S. Office Action for U.S. Appl. No. 14/858,741 dated Dec. 1, 2016.
U.S. Office Action for U.S. Appl. No. 15/289,944 dated Feb. 9, 2017.
U.S. Office Action for U.S. Appl. No. 15/336,545 dated Dec. 19, 2016.
U.S. Office Action for U.S. Appl. No. 15/453,441 dated Jun. 5, 2017.
U.S. Office Action in U.S. Appl. No. 14/193,007 dated Apr. 24, 2017.
U.S. Office Action in U.S. Appl. No. 14/656,617 dated Apr. 4, 2017.
U.S. Office Action in U.S. Appl. No. 14/609,325 dated Feb. 16, 2017.
U.S. Office Action in U.S. Appl. No. 13/480,569 dated Jul. 30, 2014.
U.S. Office Action in U.S. Appl. No. 14/193,007 dated Dec. 21, 2015.
U.S. Office Action in U.S. Appl. No. 14/193,007 dated Jul. 1, 2016.
U.S. Office Action in U.S. Appl. No. 14/193,007 dated Oct. 21, 2016.
U.S. Office Action in U.S. Appl. No. 14/193,007 dated Mar. 23, 2017.
U.S. Office Action in U.S. Appl. No. 14/656,190 dated Aug. 29, 2016.
U.S. Office Action in U.S. Appl. No. 14/656,580 dated Jun. 2, 2016.
U.S. Office Action in U.S. Appl. No. 14/656,580 dated Feb. 9, 2017.
U.S. Office Action in U.S. Appl. No. 14/819,273 dated Jul. 6, 2016.
U.S. Office Action in U.S. Appl. No. 14/843,944 dated Jan. 6, 2017.
U.S. Office Action in U.S. Appl. No. 14/856,198 dated Jun. 3, 2016.
U.S. Office Action in U.S. Appl. No. 14/856,471 dated Dec. 1, 2016.
U.S. Office Action in U.S. Appl. No. 15/099,464 dated Mar. 10, 2017.
U.S. Office Action on U.S. Appl. No. 14/656,335 dated Apr. 25, 2017.
U.S. Office Action on U.S. Appl. No. 15/332,982 dated Jan. 30, 2017.
Van Der Zande et al. "Large-scale arrays of single-layer graphene resonators." Nano letters 10.12 (2010): 4869-4873.
Verdonck, P., "Plasma Etching", in Oficina de Microfabricao: Projeto e Construcao de CI's MOS, Swart, J.W., Ed., Campinas (Sao Paulo, Brazil): UNICAMP, 2006, ch. 10, p. 9.
Vlassiouk et al. "Large scale atmospheric pressure chemical vapor deposition of graphene." Carbon 54 (2013): 58-67.
Vlassiouk et al., "Versatile ultrathin nanoporous silicon nitride membranes," Proc. Natl. Acad. Sci. USA 106(50): 21039-21044 (Dec. 15, 2009).
Wadvalla, "Boosting agriculture through seawater," Nature Middle East, 1-4 (Jul. 2, 2012). Retrieved Jun. 1, 2016 from: natureasia.com/en/nmiddleeast/article/10.1038/nmiddleeast.2012.92?WT.mc_id=FBK NatureMEast].
Wang et al., "Direct Observation of a Long-Lived Single-Atom Catalyst Chiseling Atomic Structures in Graphene," Nano Lett., 2014, pp. A-F.
Wang et al., "Graphene Oxide Membranes with Tunable Permeability due to Embedded Carbon Dots." Chemical Communications 50(86): 13089-13092 (Nov. 2014; first published online Sep. 3, 2014).
Wang et al., "Porous Nanocarbons: Molecular Filtration and Electronics," Advances in Graphene Science, Edited by Mahmood Aliofkhazraei, (2013) ISBN 978-953-51-1182-5, Publisher: InTech; Chapter 6, pp. 119-160.
Wei et al., "Synthesis of N-doped graphene by chemical vapor deposition and its electrical properties", Nano Lett. 2009 9 1752-58.
Wikipedia, "Ion track." 1-12. Jun. 1, 2016. Retrieved Jun. 1, 2016 from: en.wikipedia.org/wiki/ion_track.
Xiaogan Liang et al., Formation of Bandgap and Subbands in Graphene Nanomeshes with Sub-10nm Ribbon Width Fabricated via Nanoimprint Lithography., Nano Letters, Jun. 11, 2010, pp. 2454-2460.
Xie, et al. "Controlled fabrication of high-quality carbon nanoscrolls from monolayer graphene." Nano letters 9.7 (2009): 2565-2570.
Xu et al., "Graphene Oxide-TiO2 Composite Filtration Membranes and their Potential Application for Water Purification." Carbon 62: 465-471 (Oct. 2013; first published online Jun. 21, 2013).
Xu et al., "Graphene-like Two-Dimensional Materials", Chemical Reviews 113: 3766-3798 (Jan. 3, 2013).
Yoon, "Simulations show how to turn graphene's defects into assets," SCIENCEDAILY (Oct. 4, 2016), www.sciencedaily.com/releases/2016/10/161004120428.htm.
Zabihi et al., "Formation of nanopore in a suspended graphene sheet with argon cluster bombardment: A molecular dynamics simulation study," Nuclear Instruments and Methods in Physics Research B, 343: 48-51: (available online Nov. 26, 2014).
Zan et al. "Interaction of Metals with Suspended Graphene Observed by Transmission Electron Microscopy", J. Phys. Chem. Lett., Mar. 8, 2012, 3, 953-958.
Zan et al., "Graphene Reknits Its Holes," Nano Lett. 12(8): 3936-3940 (Jul. 5, 2012).
Zhang et al. "Effect of Chemical Oxidation on the Structure of Single-Walled Carbon Nanotubes", J. Phys. Chem., Feb. 12, 2003, B 107 3712-8.
Zhang et al. "Method for anisotropic etching of graphite or graphene" Institute of Physics, Chinese Academy Of Sciences; PEOP. Rep. China; Mar. 30, 2011.
Zhang et al. "Production of Graphene Sheets by Direct Dispersion with Aromatic Healing Agents", Small, May 6, 2010, vol. 6, No. 10, 1100-1107.
Zhang et al., "Method for Anisotropic Etching of Graphite or Graphene," English Abstract Only, Institute of Physics, Chinese Academy of Sciences, Apr. 4, 2011, (2 pages).

(56) References Cited

OTHER PUBLICATIONS

Zhang et al., "Modern Thin-Film Technology" 284-285 (Metallurgical Industry Press, 1st ed. 2009) (English translation not readily available).
Zhao et al. "Two-Dimensional Material Membranes: An Emerging Platform for Controllable Mass Transport Applications," Small 10(22): 4521-4542 (Sep. 10, 2014).
Zhao et al. (2012), "Effect of SiO2 substrate on the irradiation-assisted manipulation of supported graphene: a molecular dynamics study," Nanotechnology 23(28): 285703 (Jul. 2012) (available online Jun. 25, 2012).
Zhao et al., "Drilling Nanopores in Graphene with Clusters: A Molecular Dynamics Study," J. Phys. Chem. C, 116(21): 11776-11782 (May 9, 2012).
Zhao et al., "A glucose-responsive controlled release of insulin system based on enzyme multilayers-coated mesoporous silica particles," Chem. Commun., 47: 9459-9461 (Jun. 15, 2011).
Zhao, et al. "Efficient preparation of large-area graphene oxide sheets for transparent conductive films." ACS nano 4.9 (2010): 5245-5252.
Zhou, K., et al., "One-pot preparation of graphene/ Fe3O4 composites by a solvothermal reaction," New J. Chem., 2010, 34, 2950.
Zyga "Nanoporous Graphene Could Outperform Best Commercial Water Desalination Techniques," Phys.org., Jun. 22, 2012, Retrieved from http://www.phys.org/pdf259579929.pdf [Last Accessed Dec. 3, 2014] (3 pages).
Australian Office Action in Application No. 2013235234 dated Dec. 19, 2017 (5 pages).
Chu, L., et al., "Porous graphene sandwich/poly(vinylidene fluoride) composites with high dielectric properties," Composites Science and Technology, 86, (2013), pp. 70-75.
European Extended Search Report in Application No. 15743307.9 dated Nov. 15, 2017 (14 pages).
European Extended Search Report in Application No. 15755350.4 dated Oct. 30, 2017 (9 pages).
European Extended Search Report in Application No. 15762019.6 dated Nov. 20, 2017 (12 pages).
European Extended Search Report in Application No. 15762213.5 dated Oct. 10, 2017 (8 pages).
Gu et al., "One-step synthesis of porous graphene-based hydrogels containing oil droplets for drug delivery", Royal Society of Chemistry (RSC), vol. 4, No. 7, Jan. 1, 2014, pp. 3211-3218.
Japanese Office Action in Application No. 2015-549508 dated Nov. 7, 2017 (with English translation) (2 pages).
Japanese Office Action in Application No. 2017-002652 dated Nov. 24, 2017 (with English translation) (7 pages).
Kim et al., "Selective Gas Transport Through Few-Layered Graphene and Graphene Oxide Membranes", Science, vol. 342, Oct. 4, 2013, pp. 91-95 (6 total pages).
Singapore Search Report and Written Opinion in Application No. 11201609272T dated Oct. 5, 2017 (11 pages).
U.S. Notice of Allowance in U.S. Appl. No. 15/099,464 dated Nov. 16, 2017 (5 pages).
U.S. Notice of Allowance in U.S. Appl. No. 15/332,982 dated Nov. 1, 2017 (9 pages).
U.S. Office Action in U.S. Appl. No. 14/707,808 dated Nov. 6, 2017 (27 pages).
U.S. Office Action in U.S. Appl. No. 15/099,193 dated Dec. 28, 2017 (25 pages).
U.S. Office Action in U.S. Appl. No. 15/099,304 dated Nov. 24, 2017 (23 pages).
Wang, M., et al., "Interleaved Porous Laminate Composed of Reduced Graphene Oxide Sheets and Carbon Black Spacers by In-Situ Electrophoretic Deposition," The Royal Society of Chemistry (2014), pp. 1-3.
Wimalasiri, Y., et al., "Carbon nanotube/graphene composite for enhanced capacitive deionization performance," Carbon 59 (2013), pp. 464-471.
EPO Extended Search Report for European Application No. 171684883.5 dated Jul. 25, 2017 (8 pages).

EPO Supplementary Search Report for European Application No. 15762019.6 dated Aug. 9, 2017 (16 pages).
U.S. Notice of Allowance in U.S. Appl. No. 14/610,770 dated Sep. 26, 2017. (12 pages).
U.S. Notice of Allowance in U.S. Appl. No. 15/332,982 dated Sep. 21, 2017. (5 pages).
U.S. Office Action in U.S. Appl. No. 15/099,099 dated Oct. 5, 2017 (11 pages).
U.S. Office Action in U.S. Appl. No. 15/099,447 dated Oct. 3, 2017 (21 pages).
Weisen, et al., "Fabrication of nanopores in a graphene sheet with heavy ions: a molecular dynamics study", Journal of Applied Physics 114, 234304 (2013), pp. 234304-1 to 234304-6.
European Extended Search Report in Application No. 15837617.8 dated Mar. 22, 2018 (9 pages).
Singapore Written Opinion for Appl. Ser. No. 11201607584P dated Jun. 8, 2018 (7 pages).
U.S. Non-Final Office Action for U.S. Appl. No. 15/099,410 dated Jun. 13, 2018 (15 pages).
U.S. Notice of Allowance for U.S. Appl. No. 15/453,441 dated Jun. 12, 2018 (8 pages).
U.S. Office Action for U.S. Appl. No. 15/099,056 dated May 29, 2018 (33 pages).
U.S. Office Action for U.S. Appl. No. 15/099,289 dated Jun. 7, 2018 (16 pages).
Agenor et al., "Renal tubular dysfunction in human visceral leishmaniasis (Kala-azar)," Clinical Nephrology 71(5): 492-500 (May 2009) (available online Mar. 21, 2011).
Albert et al., "Ringer's lactate is compatible with the rapid infusion of AS-3 preserved packed red blood cells," Can. J. Anaesth. 56(5): 352-356 (May 2009) (available online Apr. 2, 2009).
Aso et al., "Comparison of serum high-molecular weight (HMV) adiponectin with total adiponectin concentrations in type 2 diabetic patients with coronary artery using a novel enzyme-linked immunosorbent assay to detect HMW adiponectin," Diabetes 55(7): 1954-1960 (Jul. 2006).
Axelsson et al., "Acute hyperglycemia induces rapid, reversible increases in glomerular permeability in nondiabetic rats," Am. J. Physiol. Renal Physiol. 298(6): F1306-F1312 (Jun. 2010) (available online Mar. 17, 2010).
Bae et al., "Roll-to-roll production of 30-inch graphene films for transparent electrodes," Nature Nanotechnology 5: 574-578 (Jun. 10, 2010) (available online Jun. 20, 2010).
Bains et al., "Novel lectins from rhizomes of two Acorus species with mitogenic activity and inhibitory potential towards murine cancer cell lines," Int'l Immunopharmacol. 5(9): 1470-1478 (Aug. 2005) (available online May 12, 2005).
Bazargani et al. (2005), "Low molecular weight heparin improves peritoneal ultrafiltration and blocks complement and coagulation," Peritoneal Dialysis Int'l 25(4): 394-404 (Jul. 2005-Aug. 2005).
Bazargani, "Acute inflammation in peritoneal dialysis: experimental studies in rats. Characterization of regulatory mechanisms," Swedish Dental J. Supp. 171: 1-57, i (2005).
Beppu et al., "Antidiabetic effects of dietary administration of Aloe arborescens Miller components on multiple low-dose streptozotocin-induced diabetes in mice: investigation on hypoglycemic action and systemic absorption dynamics of aloe components," J. Ethnopharmacol. 103(3): 468-77 (Feb. 20, 2006) (available online Jan. 6, 2006).
Cohen-Tanugi et al., "Water Desalination across Nanoporous Graphene," Nano Lett., 12(7): 3602-3608 (Jul. 11, 2012) (available online Jun. 5, 2012).
Deng et al., "Renal protection in chronic kidney disease: hypoxia-inducible factor activation vs. angiotensin II blockade," Am. J. Physiol. Renal Physiol. 299(6): F1365-F1373 (Dec. 2010) (available online Sep. 29, 2010).
Freedman et al., "Genetic basis of nondiabetic end-stage renal disease," Semin. Nephrol. 30(2): 101-110 (Mar. 2010).
Garcia-Lopez et al., "Determination of high and low molecular weight molecules of icodextrin in plasma and dialysate, using gel filtration chromatography, in peritoneal dialysis patients," Peritoneal Dialysis Int'l 25(2): 181-191 (Mar. 2005-Apr. 2005).
Gnudi (2008), "Molecular mechanisms of proteinuria in diabetes," Biochem. Soc. Trans. 36(5): 946-949 (Oct. 2008).

(56) References Cited

OTHER PUBLICATIONS

Gotloib et al., "Peritoneal dialysis in refractory end-stage congestive heart failure: a challenge facing a no-win situation," Nephrol. Dialysis. Transplant. 20(Supp. 7): vii32-vii36 (Jul. 2005).

Huang et al., "Gene expression profile in circulating mononuclear cells afterexposure to ultrafine carbon particles," Inhalation Toxicol. 22(10): 835-846 (Aug. 2010).

Jiang et al., "Porous Graphene as the Ultimate Membrane for Gas Separation," Nano Lett. 9(12): 4019-4024 (Dec. 9, 2009) (available online Sep. 23, 2009).

Jiao et al., "Castration differentially alters basal and leucine-stimulated tissue protein synthesis in skeletal muscle and adipose tissue," Am. J. Physiol. Endocrinol. Metab. 297(5): E1222-1232 (Nov. 2009) (available online Sep. 15, 2009).

Kang et al., "Effect of eplerenone, enalapril and their combination treatment on diabetic nephropathy in type II diabetic rats," Nephrol. Dialysis Transplant. 24(1): 73-84 (Jan. 2009).

Kar et al., "Effect of glycation of hemoglobin on its interaction with trifluoperazine," Protein J. 25(3): 202-211 (Apr. 2006) (available online Jun. 6, 2006).

Karan et al., "Ultrafast Viscous Permeation of Organic Solvents Through Diamond-Like Carbon Nanosheets," Science 27(335): 444-447 (Jan. 27, 2012).

Kawamoto et al., "Serum high molecular weight adiponectin is associated with mild renal dysfunction in Japanese adults," J. Atherosclerosis Thrombosis 17(11): 1141-1148 (Nov. 27, 2011).

Kim et al., "Fabrication and Characterization of Large Area, Semi-conducting Nanoperforated Graphene Materials," Nano Lett. 10(4): 1125-1131 (Apr. 2010) (available onliny Mar. 1, 2010).

Kumar et al., "Modulation of alpha-crystallin chaperone activity in diabetic rat lens by curcumin," Molecular Vision 11: 561-568 (Jul. 26, 2005).

Liu et al., "Graphene Oxidation: Thickness-Dependent Etching and Strong Chemical Doping," Nano Lett. 2008 8(7): 1965-1970 (Jun. 9, 2008) (available Jun. 19, 2008).

Mishra et al., "Functionalized Graphene Sheets For Arsenic Removal And Desalination Of Sea Water," Desalination 282: 39-45 (Jan. 13, 2011)(available online Feb. 11, 2011).

Morse (Apr. 30, 2010) Review of Kim et al. (Mar. 1, 2010) "Fabrication and Characterization of Large-Area, Semiconducting Nanoperforated Graphene Materials," InterNano Resources for Nanomanufacturing.

Nair et al. "Unimpeded Permeation of Water Through Helium-Leaktight Graphene-Based Membranes," Science 27(335): 442-444 (Jan. 27, 2012).

Nezlin, "Circulating non-immune IgG complexes in health and disease," Immunol. Lett. 122(2); 141-144 (Feb. 21, 2009) (available online Feb. 2, 2009).

Norata et al., "Plasma adiponectin levels in chronic kidney disease patients: relation with molecular inflammatory profile and metabolic status," Nutr. Metab. Cardiovasc. Dis. 20(1): 56-63 (Jan. 2010) (available online Apr. 9, 2009).

Ogawa et al., "Exosome-like vesicles in Gloydius blomhoffii blomhoffii venom," Toxicon 51(6): 984-993 (May 2008) (available online Feb. 19, 2008).

Oki et al., "Combined acromegaly and subclinical Cushing disease related to high-molecular-weight adrenocorticotropic hormone," J. Neurosurg. 110(2): 369-73 (Feb. 2009).

Osorio et al., "Effect of treatment with losartan on salt sensitivity and SGLT2 expression in hypertensive diabetic rats," Diabetes Res. Clin. Pract. 86(3): e46-e49 (Dec. 2009) (available online Oct. 2, 2009).

Osorio et al., "Effect of phlorizin on SGLT2 expression in the kidney of diabetic rats," J. Nephrol. 23(5): 541-546 (Sep.-Oct. 2010).

Padidela et al., "Elevated basal and post-feed glucagon-like peptide 1 (GLP-1) concentrations in the neonatal period," Eur. J. Endocrinol. 160(1): 53-58 (Jan. 2009) (available online Oct. 24, 2008).

Paul, "Creating New Types of Carbon-Based Membranes," Science 27(335): 413-414 (Jan. 27, 2012).

Ribeiro et al., "Binary Mutual Diffusion Coefficients of Aqueous Solutions of Sucrose, Lactose, Glucose, and Fructose in the Temperature Range from (298.15 to 328.15) K," J. Chem. Eng. Data 51(5): 1836-1840 (Sep. 2006) (available online Jul. 20, 2006).

Rippe et al., "Size and charge selectivity of the glomerular filter in early experimental diabetes in rats," Am. J. Physiol. Renal Physiol. 293(5): F1533-F1538 (Nov. 2007)(available online Aug. 15, 2007).

Sethna et al., "Serum adiponectin levels and ambulatory blood pressure monitoring in pediatric renal transplant recipients," Transplantation 88(8): 1030-1037 (Oct. 27, 2009).

Sint et al., "Selective Ion Passage through Functionalized Graphene Nanopores," J. Am. Chem. Soc. 130(49): 16448-16449 (Dec. 10, 2008) (available online Nov. 14, 2008).

Suk et al. "Water Transport Through Ultrathin Graphene," J. Phys. Chem. Lett. 1(10): 1590-1594 (May 20, 2010) (available online Apr. 30, 2010).

Sullivan et al., "Microarray analysis reveals novel gene expression changes associated with erectile dysfunction in diabetic rats," Physiol. Genom. 23(2): 192-205 (Oct. 17, 2005) (available online Aug. 23, 2005).

Takata et al. (2008),"Hyperresistinemia is associated with coexistence of hypertension and type 2 diabetes," Hypertension 51. 2 (Feb. 2008): 534-9.

Tamborlane et al. (2008),"Continuous Glucose Monitoring and Intensive Treatment of Type 1 Diabetes"; N Engl J Med 359;14: 1464-1476.

Totani et al. (2008),"Gluten binds cytotoxic compounds generated in heated frying oil ," Journal of oleo science 57. 12 (2008): 683-90.

Tsukamoto et al. (2008),"Purification, characterization and biological activities of a garlic oliqosaccharide," Journal of UOEH 30. 2 (Jun. 1, 2008): 147-57.

U.S. Notice of Allowance for U.S. Appl. No. 13/923,503 dated Oct. 14, 2016.

U.S. Notice of Allowance for U.S. Appl. No. 13/923,503 dated Oct. 5, 2016.

U.S. Office Action for U.S. Appl. No. 13/923,503 dated Mar. 22, 2016.

Vallon (2009),"Micropuncturing the nephron," Pflugers Archiv : European journal of physiology 458. 1 (May 2009): 189-201.

Vriens et al. (2010),"Methodological considerations in quantification of oncological FOG PET studies," European journal of nuclear medicine and molecular imaging 37. 7 (Jul. 2010): 1408-25.

Wang et al. (2008),"What is the role of the second "structural" NADP+-binding site in human glucose 6-phosphate dehydrogenase?,"Protein science a publication of the Protein Society 17. 8 (Aug. 2008): 1403-11.

Xie et al. (2008),"Fractionation and characterization of biologically-active polysaccharides from Artemisia tripartite," Phytochemistry 69. 6 (Apr. 2008): 1359-71.

Yagil et al. (2005),"Nonproteinuric diabetes-associated nephropathy in the Cohen rat model of type 2 diabetes," Diabetes 54. 5 (May 2005): 1487-96.

Zhang et al. (2007),"Isolation and activity of an alpha-amylase inhibitor from white kidney beans," Yao xue xue bao =Acta pharmaceutica Sinica 42. 12 (Dec. 2007): 1282-7.

Zhu et al. (2011 ),"Carbon Nanotubes in Biomedicine and Biosensing," in Carbon Nanotubes—Growth and Applications, Ch. 6, pp. 135-162.

Ziegelmeier et al. (2008),"Adipokines influencing metabolic and cardiovascular disease are differentially regulated in maintenance hemodialysis," Metabolism: clinical and experimental 57. 10 (Oct. 2008): 1414-21.

Zirk et al. (2007),"A refractometry-based glucose analysis of body fluids," Medical engineering & physics 29. 4 (May 2007): 449-58.

Chen et al., "Hierarchically porous graphene-based hybrid electrodes with excellent electrochemical performance", Journal of Materials Chemistry A: Materials for Energy and Sustainability, vol. 1, No. 33, Jan. 1, 2013, pp. 9409-9413.

Chinese Office Action in Application No. 201580006829.5 dated Jan. 23, 2018 (with English translation) (13 pages).

European Extended Search Report in Application No. 15786691.4 dated Dec. 1, 2017 (10 pages).

(56) References Cited

OTHER PUBLICATIONS

European Extended Search Report in Application No. 15789852.9 dated Dec. 6, 2017 (8 pages).
Japanese Office Action in Application No. 2017-042023 dated Jan. 9, 2018 (with English translation) (9 pages).
Singapore Search Report and Written Opinion in Application No. 11201701654U dated Dec. 6, 2017 (6 pages).
Taiwanese Office Action in Application No. 102146079 dated Dec. 12, 2017 (with English translation) (4 pages).
U.S. Notice of Allowance in U.S. Appl. No. 14/843,944 dated Feb. 9, 2018 (9 pages).
U.S. Office Action for U.S. Appl. No. 15/099,482 dated Feb. 23, 2018 (9 pages).
U.S. Office Action in U.S. Appl. No. 14/609,325 dated Jan. 16, 2018 (11 pages).
U.S. Office Action in U.S. Appl. No. 14/656,190 dated Jan. 10, 2018 (14 pages).
U.S. Office Action in U.S. Appl. No. 14/856,471 dated Jan. 11, 2018 (36 pages).
U.S. Office Action in U.S. Appl. No. 15/099,099 dated Feb. 15, 2018 (13 pages).
U.S. Office Action in U.S. Appl. No. 15/099,588 dated Feb. 1, 2018 (6 pages).
Wang et al., "Preparation of high-surface-area carbon nanoparticle/graphene composites", Carbon, Elsevier, Oxford, GB, vol. 50, No. 10, Apr. 8, 2012, pp. 3845-3853.
Office Action for Indian Appl. Ser. No. 1566/DELNP/2013 dated Feb. 2, 2018 (7 pages).
Office Action for Japanese Appl. Ser. No. 2016-521448 dated Mar. 16, 2018 (5 pages).
Skrzypek et al., "Pancreatic islet macroencapsulation using microwell porous membranes", Scientific Reports, 7: 9186 | DOI:10.1038/s41598-017-09647-7, Aug. 23, 2017 (12 pages).
U.S. Notice of Allowance for U.S. Appl. No. 15/099,464 dated Feb. 28, 2018 (5 pages).
U.S. Office Action for U.S. Appl. No. 15/099,276 dated Mar. 22, 2018 (13 pages).
U.S. Office Action for U.S. Appl. No. 15/453,441 dated Mar. 22, 2018 (7 pages).
AU Examination Report for Australian Patent Application No. 2013363283, dated Jun. 20, 2017, 4 pages.
International Search Report and Written Opinion dated Jul. 5, 2017 from related PCT application PCT/US2017/024147.
JP Office Action in Japanese Application No. 2015-501729 dated Jun. 20, 2017 (English translation).
U.S. Office Action for U.S. Appl. No. 14/656,657 dated Jul. 7, 2017.
CN Office Action in Chinese Application No. 201580006829.5 dated Aug. 1, 2017. (English translation) (8 pages).
EP Office Action for European Application No. 15743307.9 dated Aug. 8, 2017. (17 pages).
European Search Report dated Aug. 28, 2017 from related EP application 15743750.0. (7 pages).
International Search Report and Written Opinion dated Aug. 14, 2017 from related PCT application PCT/US2017/031537. (12 pages).
Jiang, L. et al., Design of advanced porous grapheme materials: from grapheme nanomesh to 3D architectures. Nanoscale, Oct. 16, 2013, vol. 6, pp. 1922-1945.
JP Office Action in Japanese Application No. 2015-503405 dated Jun. 28, 2017. (English translation) (6 pages).
JP Office Action in Japanese Application No. 2015-549508 dated Jun. 27, 2017 (English translation).
Li, R.H. "Materials for immunoisolated cell transplantation". Adv. Drug Deliv. Rev. 33, 87-109 (1998).
Schweitzer, Handbook of Separation Techniques for Chemical Engineers, 1979, McGraw-Hill Book Company, pp. 2-5 to 2-8.
Search Report and Written Opinion dated Aug. 14, 2017 for Singapore Application No. 11201606287V. (10 pages).
Search Report and Written Opinion dated Aug. 22, 2017 for Singapore Application No. 11201607584P. (7 pages).
Sears et al., "Recent Developments in Carbon Nanotube Membranes for Water Purification and Gas Separation" Materials, vol. 3 (Jan. 4, 2010), pp. 127-149.
U.S. Notice of Allowance in U.S. Appl. No. 14/193,007 dated Sep. 6, 2017. (9 pages).
U.S. Notice of Allowance in U.S. Appl. No. 14/656,580 dated Sep. 5, 2017. (8 pages).
U.S. Office Action for U.S. Appl. No. 14/609,325 dated Aug. 25, 2017. (7 pages).
U.S. Office Action for U.S. Appl. No. 15/099,193 dated Jul. 19, 2017. (13 pages).
U.S. Office Action for U.S. Appl. No. 15/289,944 dated Jul. 13, 2017. (18 pages).
U.S. Office Action for U.S. Appl. No. 15/332,982 dated Aug. 18, 2017. (9 pages).
U.S. Final Office Action for U.S. Appl. No. 14/609,325 dated Sep. 12, 2018 (8 pages).
U.S. Final Office Action for U.S. Appl. No. 15/099,289 dated Oct. 15, 2018 (14 pages).
U.S. Non-Final Office Action for U.S. Appl. No. 14/656,657 dated Oct. 10, 2018 (6 pages).
U.S. Non-Final Office Action for U.S. Appl. No. 14/707,808 dated Nov. 15, 2018 (34 pages).
U.S. Non-Final Office Action for U.S. Appl. No. 15/099,099 dated Sep. 27, 2018 (13 pages).
U.S. Non-Final Office Action for U.S. Appl. No. 15/099,269 dated Oct. 5, 2018 (11 pages).
U.S. Non-Final Office Action for U.S. Appl. No. 15/099,276 dated Nov. 1, 2018 (13 pages).
U.S. Notice of Allowance for U.S. Appl. No. 15/099,056 dated Nov. 16, 2018 (8 pages).
Bose et al.," Microfabricated immune-isolating devices for transplanting therapeutic cells in vivo", Koch Institute of Integrative Cancer Research, Massachusetts Institute of Technology, Undated (1 page).
Indian Office Action for Appl. Ser. No. 7731/DELNP/2014 dated Jul. 26, 2018 (6 pages).
Japanese Office Action for Appl. Ser. No. 2017-002652 dated Jul. 3, 2018 (8 pages).
Linnert, "Welding Metallurgy—Carbon and Alloy Steels", vol. I—Fundamentals (4th Edition), Chapter 2—The Structure of Metals, GML Publications, American Welding Society (AWS), Year: 1994, pp. 17-74. Retrieved from app.knovel.com/hotlink/pdf/id:kt0095RCL3/welding-metallurgy-carbon/structure-metals.
U.S. Final Office Action for U.S. Appl. No. 14/707,808 dated Jun. 27, 2018 (28 pages).
U.S. Final Office Action for U.S. Appl. No. 15/099,482 dated Aug. 27, 2018 (10 pages).
U.S. Non-Final Office Action for U.S. Appl. No. 15/099,239 dated Jul. 12, 2018 (31 pages).
U.S. Non-Final Office Action for U.S. Appl. No. 15/099,304 dated Aug. 27, 2018 (22 pages).
U.S. Notice of Allowance for U.S. Appl. No. 15/099,420 dated Aug. 8, 2018 (8 pages).
Vatanpour et al., "Fabrication and characterization of novel antifouling nanofiltration membrane prepared from oxidized multiwalled carbon nanotube/polyethersulfone nanocomposite", Journal of Membrane Science, vol. 375, Elsevier, Apr. 6, 2011, pp. 284-294.
Zhang et al., "Synergetic effects of oxidized carbon nanotubes and graphene oxide on fouling control and anti-fouling mechanism of polyvinylidene fluoride ultrafiltration membranes", Journal of Membrane Science, vol. 448, Elsevier, Aug. 7, 2013, pp. 81-92.
Anasori et al., "2D metal carbides and nitrides (MXenes) for energy storage", Nature Reviews, vol. 2, Article No. 16098, Jan. 17, 2017, pp. 1-17.
Australian Office Action for Appl. Ser. No. 2018200090 dated Apr. 30, 2019 (4 pages).
Huang et al., "Ultrathin Carbon Molecular Sieve Films and Room-Temperature Oxygen Functionalization for Gas-Sieving", ACS Applied Maters & Interfaces 2019, vol. 11, Apr. 16, 2019, pp. 16729-16736.
Japanese Office Action for Appl. Ser. No. 2016-566751 dated Jun. 7, 2019 (8 pages).

(56) References Cited

OTHER PUBLICATIONS

Mojtabavi et al., "Single-Molecule Sensing Using Nanopores in Two-Dimensional Transition Metal Carbide (MXene) Membranes", American Chemical Society, ACS Nano 2019, vol. 13, Mar. 7, 2019, pp. 3042-3053.
Neumann et al., "Bottom-Up Synthesis of Graphene Monolayers with Tunable Crystallinity and Porosity", American Chemical Society, ACS Nano, May 21, 2019, pp. A-M (13 pages).
Pang et al., "Applications of 2D MXenes in energy conversion and storage systems", Chemical Society Review, 2019, vol. 48, No. 1, Jun. 25, 2018, pp. 72-133.
U.S. Advisory Action for U.S. Appl. No. 15/099,239 dated Jun. 1, 2019 (7 pages).
U.S. Final Office Action for U.S. Appl. No. 14/707,808 dated Jun. 26, 2019 (37 pages).
U.S. Non-Final Office Action for U.S. Appl. No. 15/308,351 dated Jun. 30, 2019 (9 pages).
U.S. Notice of Allowance for U.S. Appl. No. 15/099,269 dated Jun. 6, 2019 (8 pages).
U.S. Appl. No. 61/452,704, filed Mar. 15, 2011, Russo et al.
Apel et al. "Effect of nanosized surfactant molecules on the etching of ion tracks: New degrees or freedom in design of pore shape", Nuclear Instruments and Methods in Physics Research Section B: Beam Interactions with Materials and Atoms, vol. 209, Aug. 2003, pp. 329-334.
Australian Office Action for Appl. Ser. No. 2015252784 dated Mar. 25, 2019 (11 pages).
Australian Office Action for Appl. Ser. No. 2015255756 dated Feb. 22, 2019 (5 pages).
Extended European Search Report for Appl. Ser. No. 16833430.8 dated Apr. 25, 2019 (11 pages).
Extended European Search Report for Appl. Ser. No. 16833432.4 dated Apr. 16, 2019 (14 pages).
Extended European Search Report for Appl. Ser. No. 16833433.2 dated Mar. 4, 2019 (15 pages).
International Search Report and Written Opinion for PCT Appl. Ser. No. PCT/US2018/065514 (16 pages), dated Mar. 18, 2019.
Japanese Office Action for Appl. Ser. No. 2016-565216 dated Feb. 26, 2019 (7 pages).
Kim et al., "High quality reduced graphene oxide through repairing with multi-layered graphene ball nanostructures", Scientific Reports, vol. 3, No. 1, Nov. 19, 2013, pp. 1-6.
Singapore Written Opinion for Appl. Ser. No. 11201800845X dated Feb. 26, 2019 (8 pages).
Singapore Written Opinion for Appl. Ser. No. 11201800883R dated Feb. 22, 2019 (7 pages).
Singapore Written Opinion for Appl. Ser. No. 11201800968Q dated Feb. 19, 2019 (6 pages).
U.S. Final Office Action for U.S. Appl. No. 15/099,269 dated Apr. 18, 2019 (7 pages).
U.S. Final Office Action for U.S. Appl. No. 15/099,304 dated Apr. 19, 2019 (27 pages).
U.S. Non-Final Office Action for U.S. Appl. No. 14/656,657 dated Mar. 28, 2019 (9 pages).
U.S. Non-Final Office Action for U.S. Appl. No. 14/686,452 dated May 3, 2019 (7 pages).
U.S. Non-Final Office Action for U.S. Appl. No. 15/099,193 dated May 2, 2019 (19 pages).
Canadian Office Action for Appl. Ser. No. 2,865,648 dated Jan. 16, 2019 (4 pages).
EPO Office Action for Appl. Ser. No. 13714806.0 dated Dec. 5, 2018 (6 pages).
EPO Office Action for Appl. Ser. No. 15786691.4 dated Dec. 5, 2018 (6 pages).
Extended European Search Report for Appl. Ser. No. 16833431.6 dated Feb. 25, 2019 (16 pages).
Koenig et al., "Selective Molecular Sieving Through Porous Graphene", Nature Nanotechnology, vol. 7, No. 11, pp. 728-732 (Including Supplementary Informaton) (23 pages), (2012).
U.S. Advisory Action for U.S. Appl. No. 15/099,289 dated Jan. 8, 2019 (6 pages).
U.S. Final Office Action for U.S. Appl. No. 14/686,452 dated Dec. 13, 2018 (6 pages).
U.S. Final Office Action for U.S. Appl. No. 15/099,099 dated Jan. 2, 2019 (13 pages).
U.S. Final Office Action for U.S. Appl. No. 15/099,239 dated Feb. 21, 2019 (26 pages).
U.S. Non-Final Office Action for U.S. Appl. No. 14/609,325 dated Jan. 14, 2019 (7 pages).
U.S. Non-Final Office Action for U.S. Appl. No. 15/099,482 dated Jan. 31, 2019 (13 pages).
U.S. Notice of Allowance for U.S. Appl. No. 15/099,289 dated Jan. 18, 2019 (7 pages).
U.S. Notice of Allowance for U.S. Appl. No. 15/099,410 dated Jan. 3, 2019 (9 pages).
Extended European Search Report for Appl. Ser. No. 16833429.0 dated Aug. 9, 2019 (14 pages).
Farah et al., "Long-Term Implant Fibrosis Prevention in Rodents and Non-Human Primates Using Crystallized Drug Formulations", Nature Materials, vol. 18, Aug. 2019, pp. 892-904.
Japanese Office Action for Ser. Appl. No. 2017-511982 dated Jul. 9, 2019 (6 pages).
Raimondo et al., "Functional muscle recovery with nanoparticle-directed M2 macrophage polarization in mice", Proceedings of the National Academy of Sciences of the United States of America (PNAS), Sep. 4, 2018, pp. 1-6.
University of Massachusetts Medical School, "Fibrosis Mitigation Pathway", PowerPoint Presentation, date of presentation unknown (6 pages).
U.S. Non-Final Office Action for U.S. Appl. No. 15/589,135 dated Aug. 1, 2019 (11 pages).
U.S. Notice of Allowance for U.S. Appl. No. 14/609,325 dated Jul. 30, 2019 (7 pages).
Yang et al., "Large-area graphene-nanomesh/carbon-nanotube hybrid membranes for ionic and molecular nanofiltration", Science, vol. 364, Jun. 14, 2019, pp. 1057-1062 (7 pages).
Zhang et al., "Rapid and Long-Term Glycemic Regulation with a Balanced Charged Immune-Evasive Hydrogel in T1DM Mice", Advanced Functional Materials, Advanced Science News, Jan. 30, 2019, pages 1-9.
Zhang et al., "Rapid and Long-Term Glycemic Regulation with a Balanced Charged Immune-Evasive Hydrogel in T1DM Mice", Advanced Functional Materials, Advanced Science News, Jan. 30, 2019, Supporting Information (13 pages).

GRAPHENE-BASED FILTER FOR ISOLATING A SUBSTANCE FROM BLOOD

CROSS-REFERENCE TO RELATED PATENT APPLICATIONS

This application is a continuation of U.S. application Ser. No. 13/923,503, filed Jun. 21, 2013, which issued as U.S. Pat. No. 9,572,918 on Feb. 21, 2017, each of which is incorporated by reference herein in its entirety.

TECHNICAL FIELD

This disclosure relates to systems and methods for isolating a substance from a solution. In particular, this disclosure describes systems and methods for using multiple graphene-based filters to isolate a substance from blood.

BACKGROUND

Blood includes several constituents ranging in size. For example, hemoglobin has an effective molecular radius of 3.25 nanometers (nm) and sodium has an effective molecular radius of 0.10 nm. Substances having particles with a size within the range of blood constituents may be harmful when they are dissolved or suspended in blood. For example, certain viruses and toxics are sized within the range of constituents of blood. Further, some individuals may have conditions that lead to elevated amounts of regularly occurring constituents. Elevated amounts of regularly occurring blood constituents may be unhealthy to individuals. For example, diabetes is a metabolic disease that may lead to elevated levels of glucose. Elevated levels of glucose may lead to serious complications, such as organ failure.

In order to control blood sugar levels, diabetics may follow a strict diet regimen or inject insulin. However, insulin injections do not literally remove sugar from the blood. Insulin opens cell walls to allow glucose to enter where it is converted to glycogen and fat. Thus, insulin injections may lead to obesity, which may aggravate diabetes and increase the risk of other diseases, such as heart disease, colon cancer, and hypertension.

SUMMARY

In general, this disclosure relates to systems and methods for isolating a substance from a solution. In particular, this disclosure describes systems and methods for using multiple graphene-based filters to isolate a substance having particles sized within the constituents of blood from a bloodstream. The substance may be a constituent of blood occurring at an elevated level or a foreign substance. The techniques of this disclosure may be used for the treatment of diseases, such as, for example diabetes. In one example, the techniques of this disclosure may be applied to remove excess glucose from the blood. The techniques of this disclosure may allow for non-hormonal glucose control, thereby preventing excess glucose from being converted to glycogen and fat. Although the techniques of this disclosure are described with respect to blood and example substances, the techniques of this disclosure may be generally applied to isolating particles or molecules of one species from a solution or suspension containing both larger and smaller particles or molecules.

According to one example of this disclosure a device for isolating a substance from blood, wherein particles of the substance have an effective diameter that is within a range defined by effective diameters of constituents of blood, the device comprises a first sheet of graphene including a first plurality of apertures, wherein the first plurality of apertures are configured to pass objects with an effective diameter less than or equal to the effective diameter of the particles of the substance, a second sheet of graphene including a second plurality of apertures, wherein the second plurality of apertures are configured to pass objects with an effective diameter less than the effective diameter of the particles of the substance, and a conduit system coupled to the first sheet of graphene and the second sheet of graphene, wherein the conduit system is configured to isolate the particles of the substance as blood flows through the conduit system.

According to one example of this disclosure a device for isolating a substance from blood, wherein particles of the substance have an effective diameter that is within a range defined by effective diameters of constituents of blood, comprises a first sheet of graphene including a first plurality of apertures, wherein the first plurality of apertures are configured to pass objects with an effective diameter less than or equal to the effective diameter of the particles of the substance, a second sheet of graphene including a second plurality of apertures, wherein the second plurality of apertures are configured to pass objects with an effective diameter less than the effective diameter of the particles of the substance, and a mechanical system coupled to the first sheet of graphene and the second sheet of graphene, wherein the mechanical system is configured to isolate the particles of the substance using a reversible cycle.

According to one example of the disclosure, a method for isolating a substance from blood, wherein particles of the substance have an effective diameter that is within a range defined by effective diameters of constituents of blood, comprises regulating the flow of the blood through a first sheet of graphene including a first plurality of apertures, wherein the first plurality of apertures are configured to pass objects with an effective diameter less than or equal to the effective diameter of the particles of the substance, and regulating the flow of the blood through a second sheet of graphene including a second plurality of apertures, wherein the second plurality of apertures are configured to pass molecules with an effective diameter less than the effective diameter of the particles of the substance.

According to another example of the disclosure an apparatus configured to isolate a substance from blood, wherein particles of the substance have an effective diameter that is within a range defined by effective diameters of constituents of blood, comprises means for regulating the flow of the blood through a first sheet of graphene including a first plurality of apertures, wherein the first plurality of apertures are configured to pass objects with an effective diameter less than or equal to the effective diameter of the particles of the substance, and means for regulating the flow of the blood through a second sheet of graphene including a second plurality of apertures, wherein the second plurality of apertures are configured to pass molecules with an effective diameter less than the effective diameter of the particles of the substance.

The details of one or more examples are set forth in the accompanying drawings and the description below. Other features, objects, and advantages will be apparent from the description and drawings, and from the claims.

BRIEF DESCRIPTION OF DRAWINGS

This written disclosure describes illustrative embodiments that are non-limiting and non-exhaustive. Reference is made to illustrative embodiments that are depicted in the figures, in which.

DETAILED DESCRIPTION

Figure 1:
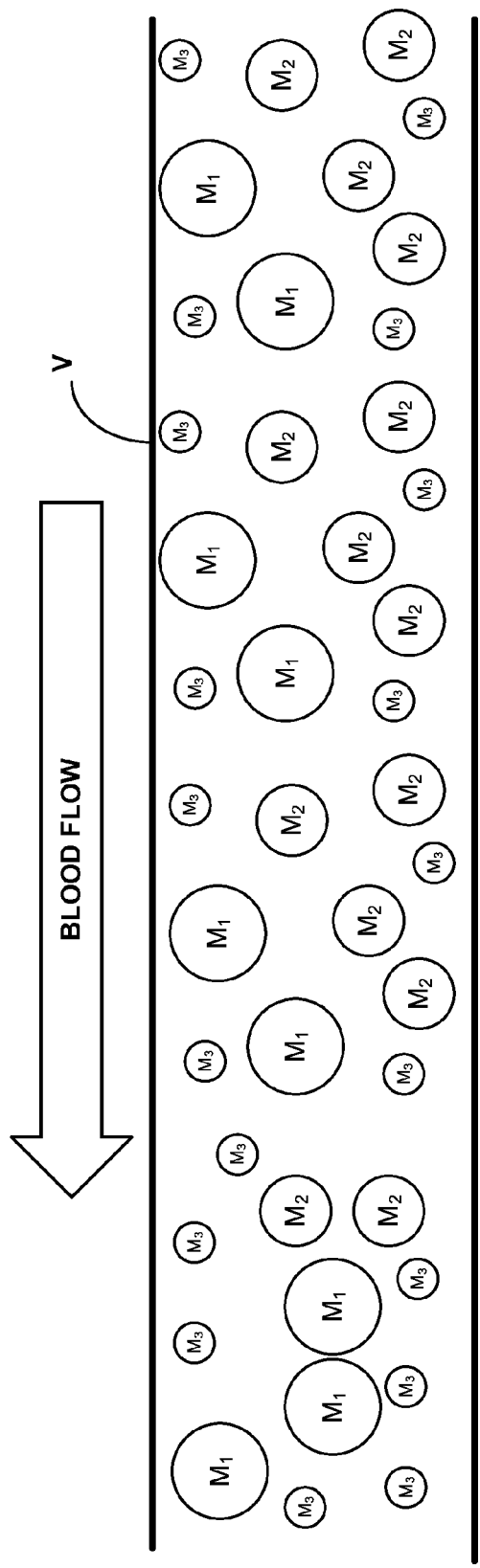
FIG. 1 is a conceptual diagram illustrating substances dissolved or suspended in the blood stream.

Molecular filtration techniques are emerging due to nanotechnology developments. Commonly assigned U.S. Pat. No. 8,361,321 (hereinafter "Stetson"), which is incorporated herein by reference in its entirety, describes using a graphene sheet with nano-sized perforations to remove unwanted ions from water. While a single graphene sheet with nano-sized perforations can be used to separate larger molecules from smaller molecules, filtration techniques that use a single molecular membrane with one perforation size may be not be able to selectively isolate an object of a particular size from objects within a band of sizes. Because blood has several regularly occurring constituents of varying sizes, filtration techniques using a single graphene sheet may not be able to remove a substance without also removing regularly occurring constituents. In the United States, 5.8 million people or 8.3% of the population suffer from diabetes. Diabetes can be treated by removing excess glucose from the bloodstream. Because glucose is sized between other constituents of blood, removing glucose from blood using a single filter may not be an effective treatment because the filter may also remove other "healthy" blood constituents. The systems and techniques described herein provide techniques for isolating particles of a substance from blood where the particles are sized within the size of the constituents of blood, such as, e.g., glucose. The systems and techniques described herein may provide effective non-hormonal treatments to diseases, such as e.g., diabetes.

Although the techniques of this disclosure are described in the examples below with respect to blood and glucose, the techniques of this disclosure may be generally applied to isolating particles or molecules of one species from a solution or suspension containing both larger and smaller particles and/or molecules. Embodiments of the present disclosure may be best understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In addition, the steps of a method do not necessarily need to be executed in any specific order, or even sequentially, nor need the steps be executed only once, unless otherwise specified. In some cases, well-known structures, materials, or operations are not shown or described in detail.

Human blood typically includes 55% plasma. Plasma is composed of 90% water and dissolved substances (e.g., sodium, chlorine, potassium, manganese, and calcium ions). The remaining 10% of plasma is composed of blood plasma proteins (e.g., albumin, globulin, and fibrinogen) and hormones. The 45% of human blood that is not composed of plasma is typically composed of 99% erythrocytes (i.e., red cells), less than 1% leucocytes (i.e., white cells), and less than 1% thrombocytes (i.e., platelets). Table 1 illustrates the relative size of constituents of blood with respect to one another. Table 1 illustrates the permselectivity of blood constituents in the glomerulus. It should be noted that the actual sizes of constituents in Table 1 may vary based on several factors (e.g., temperature) and may be expressed in several different manners. In this manner, Table 1 should not be limiting.

TABLE 1

Constituents of Blood

| Substance | Molecular Mass (g/mol) | Effective molecular radius (nm) |
|---|---|---|
| sodium | 23 | 0.10 |
| potassium | 39 | 0.14 |
| water | 18 | 0.15 |
| urea | 60 | 0.16 |
| chloride | 35.5 | 0.18 |
| glucose | 180 | 0.33 |
| sucrose | 342 | 0.44 |
| polyethylene glycol | 1 | 0.70 |
| inulin | 5.2 | 1.48 |
| myoglobin | 16.9 | 1.88 |
| lysozyme | 14.6 | 1.90 |
| lactoglobulin | 36 | 2.16 |
| egg albumin | 43.5 | 2.80 |
| hemoglobin | 68 | 3.25 |
| serum albumin | 69 | 3.55 |

This disclosure describes examples where glucose is isolated from blood. As illustrated in Table 1, glucose is physically smaller than dissolved proteins, but larger than mineral ions that are the major constituents of blood plasma. Ribeiro et al "Binary Mutual Diffusion Coefficients of Aqueous Solutions of Sucrose, Lactose, Glucose, and Fructose in the Temperature Range from (298.15 to 328.15) K," Journal of Chemical and Engineering Data, Vol. 51, No. 5, 2006, which is incorporated by reference, in its entirety, provides values for the effective hydrodynamic radius of glucose in an aqueous solution at different temperatures. Based on the values provided in Ribeiro, the examples below assume that the effective diameter of particles of glucose dissolved in blood at body temperature is approximately 0.72 nm. It should be noted that the systems and techniques described herein are not limited based on an assumed particle size of a substance. The examples below can readily be modified based on measured or predicted particle sizes. Further, the term effective diameter is used herein to describe the size of an object based on the diameter of a sphere that would encapsulate the object. It most cases the object may not actually have a spherical shape and the effective diameter may generally correspond to a length of an object.

FIG. 1 is a conceptual diagram illustrating substances dissolved or suspended in the bloodstream. In the example illustrated in FIG. 1, blood flows through vein V. In FIG. 1, $M_2$ represents particles of a substance to be isolated from the bloodstream and $M_1$ and $M_3$ respectively represent larger and smaller constituents of blood. For example, as describe above, $M_2$ may represent a dissolved glucose molecule with an effective diameter of 0.72 nm, $M_1$ may represent myoglobin with an effective diameter of 3.75 nm, and $M_3$ may represent urea with an effective diameter of 0.32 nm. In other examples, $M_2$ may be a bio-pathogen (a virus or a bacterium) or a toxin. Toxins may include, for example, heavy metals (e.g., lead) or alcohol. As described above, removing $M_2$ blood without also removing $M_1$ and $M_3$ may be difficult using conventional techniques. In some cases, removing $M_1$ or $M_3$ from a patient's bloodstream may result in more health consequences to the patient than simply leaving $M_2$ in the bloodstream.

Figure 2:
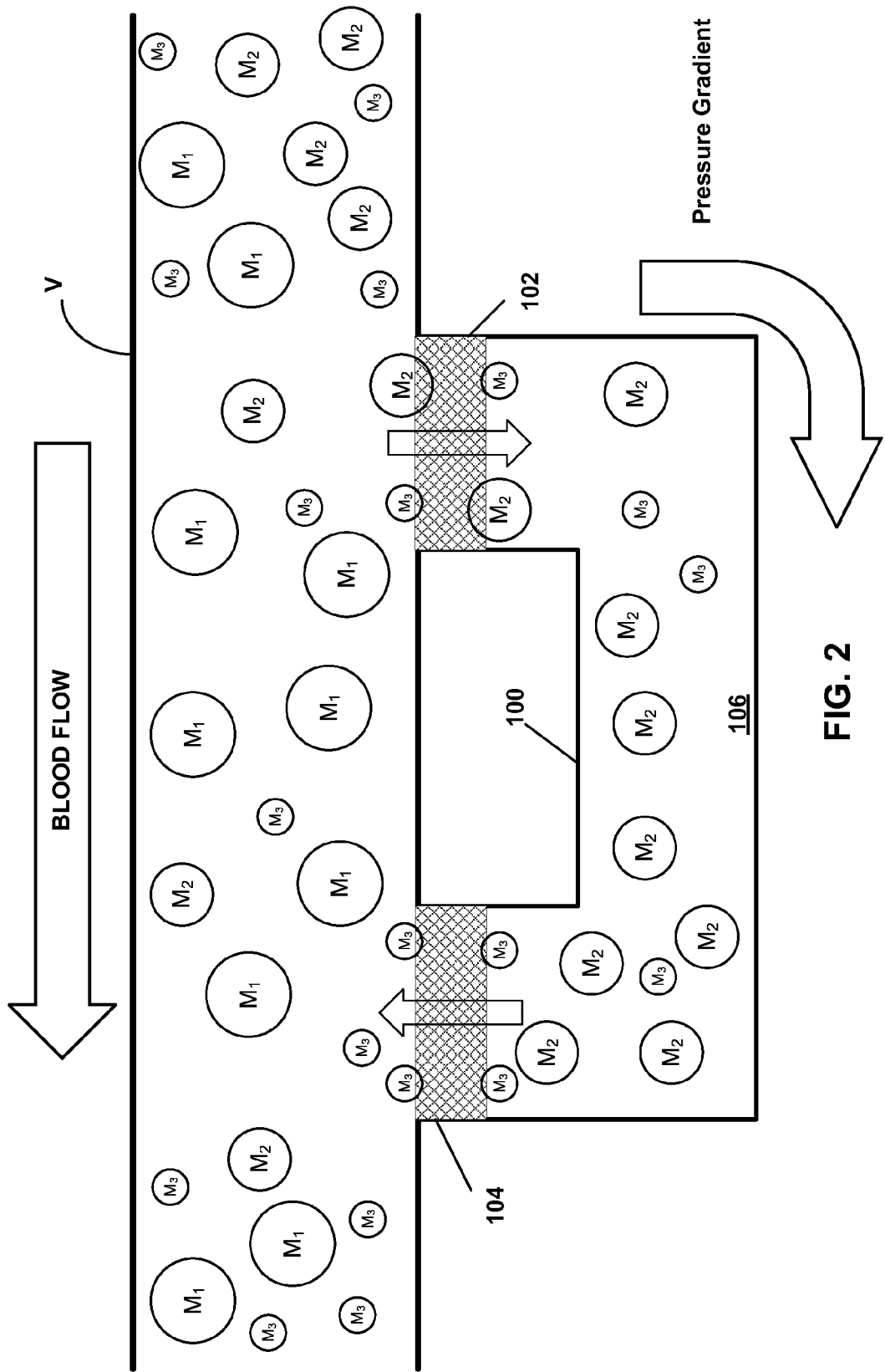
FIG. 2 is a conceptual diagram illustrating an example of two stage bypass filtering according to techniques described in this disclosure.

FIG. 2 is a conceptual diagram illustrating an example of two stage bypass filtering according to techniques described in this disclosure. The conceptual diagram illustrated in FIG. 2, illustrates an example where two stage filter 100 is configured to isolate a substance from blood. Similar to FIG. 1, particles of a substance to be isolated are illustrated as $M_2$, particles larger than $M_2$ are illustrated as $M_1$, and particles smaller than $M_2$ are illustrated as $M_3$. As illustrated in FIG. 2, two stage filter 100 is operably coupled to vein V. It should be noted that while two stage filter 100 is illustrated in FIG. 2 as being directly coupled to vein V, two stage filter 100 may be coupled to vein V using a series of one or more intermediate conduits. Further, it should be noted that while the example in FIG. 2 illustrates two stage filter 100 as being operably coupled to a vein, two stage filter 100 may be operably coupled to any part of the circulatory system (e.g., an artery).

Two stage filter 100 includes first filter 102, second filter 104, and conduit 106. Two stage filter 100 may be located outside of the body as a standalone device or may be part of an implantable medical device implanted in a patient. As illustrated in FIG. 2, as blood flows through vein V, pressure gradient causes blood to flow into conduit 106 and bypass the normal path through V. In some cases, the pressure gradient may be generated using a small pump or electromagnetic fields, thereby drawing blood into conduit 106. In other cases, the natural flow of blood through vein V and/or gravitation forces may be sufficient to cause blood to flow into conduit 106. First filter 102 is disposed at the proximal end of conduit 106. First filter 102 may be configured to pass only particles with a size less than or equal to the particles of the substance to be isolated from bloodstream. Thus, as illustrated in FIG. 2 particles larger than $M_2$, i.e., $M_1$, do not enter conduit 106. For example, if $M_2$ represents glucose particles and $M_3$ represents myoglobin particles, glucose particles and smaller particle will enter conduit 106 and myoglobin particles will continue to flow through vein V unabated. Second filter 104 is disposed at the distal end of conduit 106. Second filter 104 may be configured to only allow passage of particles with a size less than particles $M_2$, i.e., $M_3$. Thus, the particles smaller than $M_2$ that have entered conduit 106 will return to vein V, while $M_2$ particles remain in conduit 106. In this manner, $M_2$ particles are effectively isolated from the bloodstream.

As blood continues to flow through vein V, $M_2$ particles may continue to enter conduit 106 and will accumulate. Two stage filter 100 may be configured such that $M_2$ particles may be removed from conduit 106. In some examples, conduit 106 may be configured to be decoupled from two stage filter 100. In other examples, conduit 106 may be coupled to one or more valves (not shown in FIG. 2) that may be opened to remove $M_2$ particles from conduit 106. In some cases, conduit 106 may become saturated with $M_2$ particles and $M_2$ particles may be siphoned off when saturation is achieved. The process of isolating $M_2$ particles in conduit 106 and removing $M_2$ particles from conduit 106 can be repeated, as desired.

It should be noted that in some cases, based on the pressure gradient and rate of blood flow, some $M_2$ and $M_3$ particles may continue to flow through vein V unabated without entering conduit 106. However, pressure gradient may be configured such that a desired percentage of $M_2$ and $M_3$ particles flow through first filter 102 and into conduit 106. Typically there is only 5 grams of glucose is in the bloodstream of a healthy 75 kg adult with 5 liters of blood. Thus, in the case where $M_2$ is glucose, pressure gradient and two stage filter 100 may be configured to produce a known rate of filtration in order to maintain a healthy level of glucose in the bloodstream.

As described above, first filter 102 may be configured to pass only particles with a size less than or equal to the particles of the substance to be isolated from bloodstream and second filter 104 may be configured to only allow passage of particles with a size less than particles of a substance to be isolated. In one example, first filter 102 and/or second filter 104 may be a sheet of graphene including a plurality of apertures, e.g., a perforated graphene sheet. Graphene is a single-atomic-layer-thick layer of carbon atoms which may form a sheet. The carbon atoms of a graphene sheet define a repeating pattern of hexagonal ring structures (benzene rings) constructed of six carbon atoms, which form a honeycomb lattice of carbon atoms. An interstitial aperture is formed by each six carbon atom ring structure in the sheet and this interstitial aperture is much less than one nanometer across and is much too small to allow the passage of water or other blood constituents. As described in publications Liu, Li et al., "Graphene Oxidation: Thickness-Dependent Etching and Strong Chemical Doping," Nano Letters 2008; vol. 8, No. 7, Jun. 9, 2008 pg 1965-1970 and Kim et al "Fabrication and Characterization of Large Area, Semiconducting Nanoperforated Graphene Materials," Nano Letters 2010; vol. 10, No. 4, Mar. 1, 2010, pp 1125-1131, (each of which are incorporated by reference in their entirety) perforations can be made on a sheet of graphene. Perforene™ is an example trade name of a perforated graphene sheet. The techniques of this disclosure are not limited to particular techniques for making perforations on graphene and any technique, such as laser drilling, may be used to introduce perforations on a graphene sheet in accordance with the techniques described herein.

Figure 3:
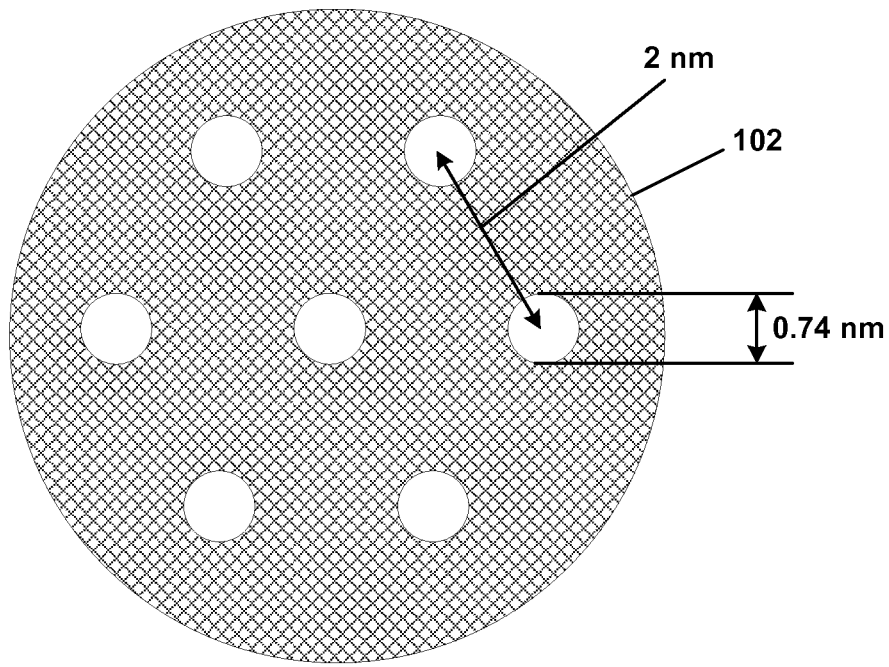
FIG. 3 is a conceptual diagram illustrating a cross-sectional view of a filter according to techniques of this disclosure.

FIG. 3 is a conceptual diagram illustrating a cross-sectional view of a filter according to techniques of this disclosure. Filter 102 is an example filter configured to pass particles of a substance in a solution without also passing larger particles in a solution. In one example, filter 102 may be a single sheet of graphene with a thickness of 2 nm. In other examples, filter 102 may include multiple sheets of graphene to achieve a desired thickness. In other examples, filter 102 may include one or more Ultra Nanocrystalline Diamond membranes. It should be noted that although the apertures of filter 102 are illustrated as having a generally round shape, the actual shape of the apertures is affected based on the method used to manufacture filter 102. For example, in the case where filter 102 is a graphene sheet the edges of the aperture may be defined, in part, by the hexagonal carbon ring structure.

In the example illustrated FIG. 3, filter 102 is configured to pass objects with an effective diameter less than or equal to the effective diameter of the particles of glucose. As described above, a particle of glucose dissolved in blood at body temperature is assumed to have an effective diameter of approximately 0.72 nm. Thus, in order to pass objects with an effective diameter less than or equal to the effective diameter of the particles of glucose, filter 102 includes a plurality of apertures with a diameter slightly larger than 0.72 nm. In the example illustrated in FIG. 3, the diameter of apertures of filter 102 are nominally 0.74 nm. That is, the diameters of the apertures of filter 102 are approximately 2-3% larger than the effective diameter of glucose. It should be noted that the diameter of the apertures of filter 102 may further be increased to more efficiently pass glucose molecules. For example, the diameter of apertures of filter 102 may be within a range that is 2%-25% larger than the effective diameter particles of a substance to be isolated.

Further, it should be noted that the diameter of the apertures of filter 102 may be increased such that a particle of a substance to be isolated passes through filter 102 and a known larger size particle of a solution does not pass through filter 102. With reference to Table 1 above, the constituent of blood sequentially larger than glucose is sucrose, which may be assumed to have an effective diameter of 0.88 nm. Thus, in the example where glucose is to be isolated from blood the size of apertures of filter 102 may be increased to slightly smaller than 0.88 nm, such that sucrose does not pass through filter 102.

In the example illustrated in FIG. 3, the apertures of filter 102 have a nominal spacing of 2 nm. In principle, the flow rate will be proportional to the aperture density. As the aperture density increases (i.e., the nominal spacing decreases), the flow through the apertures of filter 102 may will increase, but may also become "turbulent," which may adversely affect the flow at a given pressure. Further, as the aperture density increases, the strength of filter 102 may be reduced, particularly when filter 102 is a single graphene sheet. A reduction in strength may, under some circumstances, cause filter 102 to rupture. Based on the flow and strength considerations a 2 nm center-to-center spacing between apertures is believed to be near optimum when filter 102 is a sheet of graphene. However, the nominal spacing between apertures of filter 102 may be readily increased or decreased based on desired flow rates and strength characteristics of filter 102.

Figure 4:
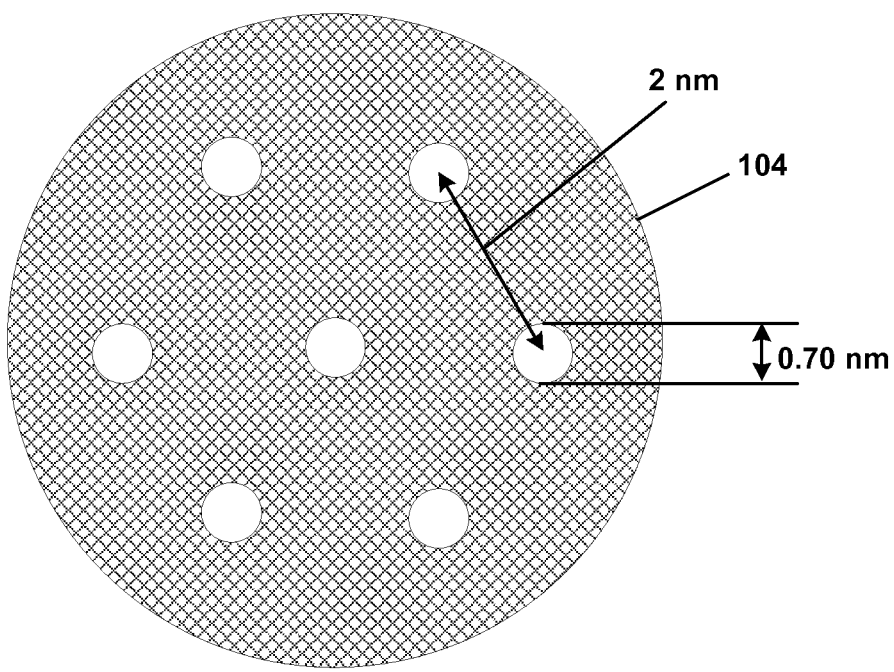
FIG. 4 is a conceptual diagram illustrating a cross-sectional view of a filter according to techniques of this disclosure.

FIG. 4 is a conceptual diagram illustrating a cross-sectional view of a filter according to techniques of this disclosure. Filter 104 may be of similar construction to filter 102 described above and for the sake of brevity construction details of filter 104 will not be described herein and reference is made to discussion of filter 102. In the example illustrated FIG. 4, filter 104 is configured to pass objects with an effective diameter less than the effective diameter of the particles of glucose, i.e. block glucose particles, while allowing smaller particles to pass through. As described above, a particle of glucose dissolved in blood at body temperature is assumed to have an effective diameter of approximately 0.72 nm. Thus, in order to pass objects with an effective diameter less than the effective diameter of the particles of glucose, filter 104 includes a plurality of apertures with a diameter slightly smaller than 0.72 nm. In the example illustrated in FIG. 3, the diameter of apertures of filter 104 are nominally 0.70 nm. That is, the diameters of the apertures of filter 104 are approximately 2-3% smaller than the effective diameter of glucose.

It should be noted that the diameter of the apertures of filter 104 may further be decreased. For example, the diameter of apertures of filter 104 may be within a range that is 2%-25% smaller than the effective diameter particles of a substance to be isolated. The diameter of the apertures of filter 104 may be decreased such that a particle of a substance to be isolated does not pass through filter 104 and a known smaller particle of a solution passes through filter 104. In some instances reducing the diameter of the apertures may increase the strength of filter 104. As illustrated in FIG. 4, the apertures of filter 104 have a nominal spacing of 2 nm. As discussed above with respect to filter 102, spacing of apertures can be determined based on a desired flow rate and a required level of strength. The spacing of the apertures of FIG. 4 may be determined based on similar characteristics. Further, the diameter of apertures of filter 104 may be determined based on similar characteristics.

Figure 5:
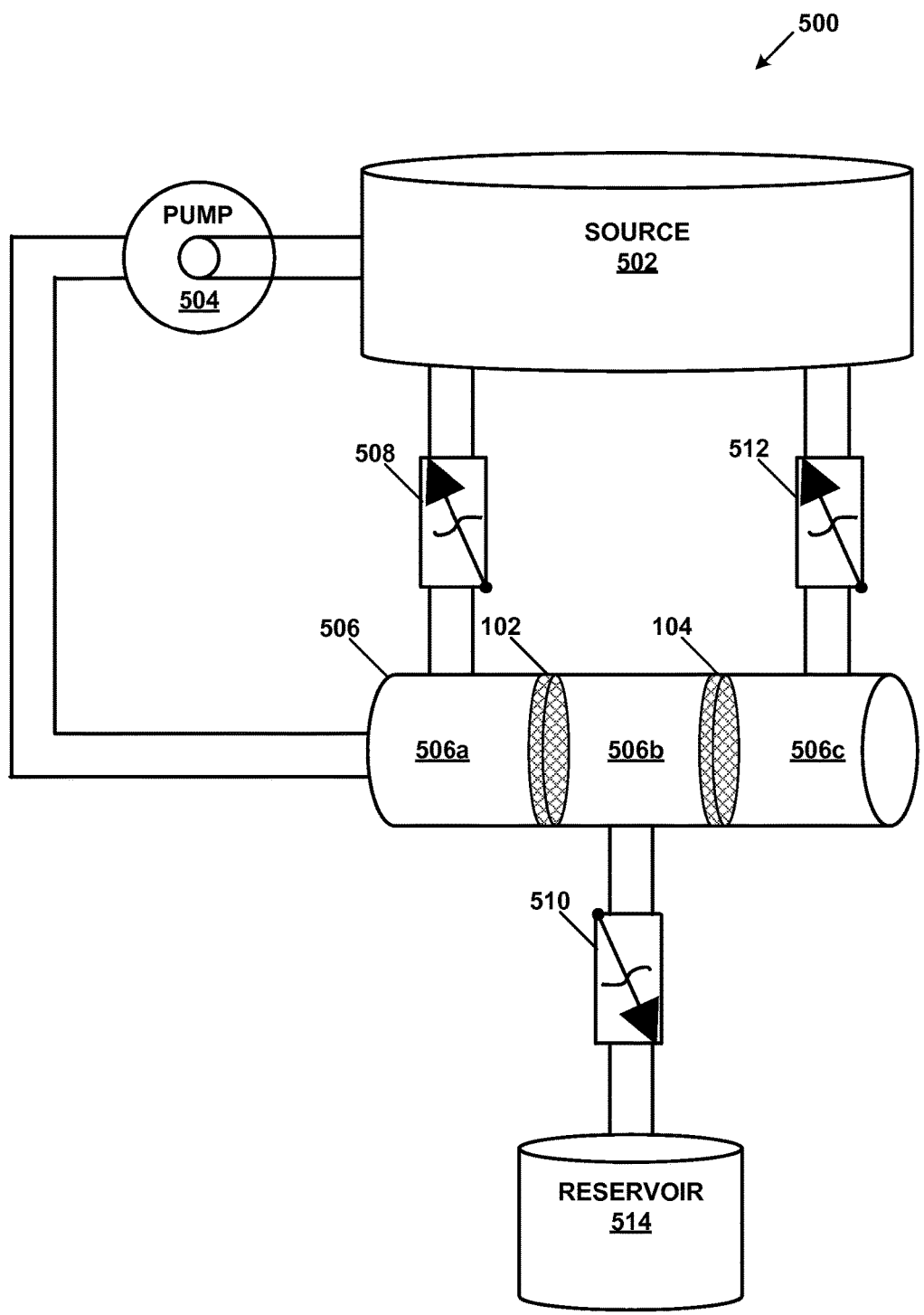
FIG. 5 is a conceptual diagram illustrating an example device for isolating a substance from a solution according to techniques of this disclosure.

FIG. 5 is a conceptual diagram illustrating an example device for isolating a substance from a solution according to techniques of this disclosure. As illustrated in FIG. 5, device 500 includes source 502, pump 504, chamber 506, pressure valve 508, pressure valve 510, pressure valve 512, and reservoir 514. Further, chamber 506 includes first section 506a, first filter 102, second section 506b, second filter 104, and third section 506c. Components of device 500 may be operably coupled as illustrated in FIG. 5.

In one example, components are connected using flexible tubes that are configured to accommodate moderate expansion of based on the volume of fluid in each section. For example, tubes may be constructed using known flexible materials, such as, rubber or plastic. Source 502 may be any container containing a solution from which a substance is to be isolated. In the example where glucose is to be isolated from blood, source 502 may be the circulatory system of a patient or an intermediate vessel containing blood drawn from a patient. Pump 504 is operably coupled to source 502 and is configured to circulate a solution from source 502 through chamber 506 and back to source 502. Pump 504 may be any type of electric, mechanical, or electromechanical pump configured to circulate a solution according to a desired flow rate. As a solution passes through chamber 506 a substance is isolated from a solution according to the general principles of two stage filtering described above with respect to FIG. 2.

As illustrated in FIG. 5, first section 506a of chamber 506 is operably coupled to pump 504, first filter 102, and pressure valve 508, which is in turn operably coupled to source 502. Pump 504 causes fluid to enter section 506a from the source 502. First filter 102 and pressure valve 508 determine which portions of solution (e.g., constituents of blood) flow into second section 506b of chamber 506 and which portions of solution circulate back to source 502. First filter 102 may be any of the example first filters described above. In the example where glucose is to be isolated from blood, first filter 102 may include a sheet of graphene including apertures sized and spaced according to the example illustrated in FIG. 3. Pressure valve 508 may be a one-way pressure release valve (also referred to as a pressure diode). Pressure valve 508 may be configured to have a pressure setting such that there is no uncontrolled pressure build-up in section 506a while solution is pumped from source 502 through first filter 102 at a given flow rate. Further, the pressure release setting of pressure release valve 508 may be set to achieve a steady-state operation based on desired flow rates of solution passing through filter 102 and solution circulating back to source 502. In the example where glucose is isolated from blood, pump 504, first filter 102, and pressure release valve 508 may be configured such that objects having a size less than or equal to the size of glucose enter second section 506b and objects have a size larger than the size of glucose circulate back to source 502, according to desired flow rates.

Objects that are able to pass through first filter 102 enter second section 506b of chamber 506. As illustrated in FIG. 5, second section 506b is operable coupled second filter 104 and pressure release valve 510. Second filter 104 may be any of the example second filters described above. In the example where glucose is to be isolated from blood, second filter 104 may include a sheet of graphene including apertures sized and spaced according to the example illustrated in FIG. 4. In this example, object having a size smaller than a glucose molecule are able to enter section 506c and subsequently return to source 502. Reservoir 514 is configured to receive objects that do not pass through filter 104, e.g., glucose molecules.

Thus, as a solution circulates through chamber 506 the substance to be isolated accumulates in reservoir 514. Pressure valves 510 and 512 may be configured such that there is no uncontrolled pressure build-up in sections 506b and 506c while solution is pumped from section 506b through second filter 104. Further, pressure release valves 510 and 512 may be configured to achieve a steady-state operation based on a desired rate of filtration. The amount of a substance in reservoir 514 may be measured in order to determine the amount of substance that has been isolated for a solution. In this manner, device 500 represents an example of a device configured to isolate a substance from a solution, wherein particles of the substance have an effective diameter that is within a range defined by effective diameters of a solution.

Figure 7:
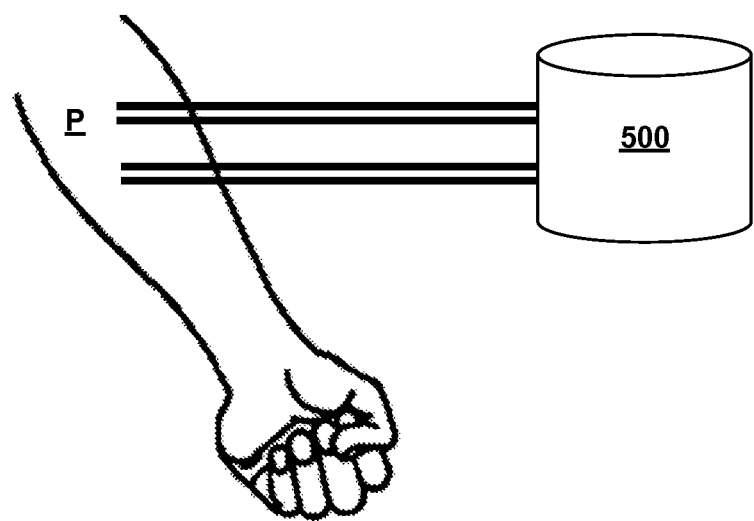
FIG. 7 is a conceptual diagram illustrating an example device for isolating a substance from blood affixed to a patient.

In some examples device 500 may be implemented as part of an external medical device or may be implemented as part of an implantable medical. FIG. 7 is a conceptual diagram illustrating an example device for isolating a substance from blood affixed to a patient. In the example, illustrated in FIG. 7 device 500 is an external medical device that is operably coupled to patient P. In this manner, device 500 is an example of a device configured to isolate a substance from blood, wherein particles of the substance have an effective diameter that is within a range defined by effective diameters of constituents of blood.

Figure 6:
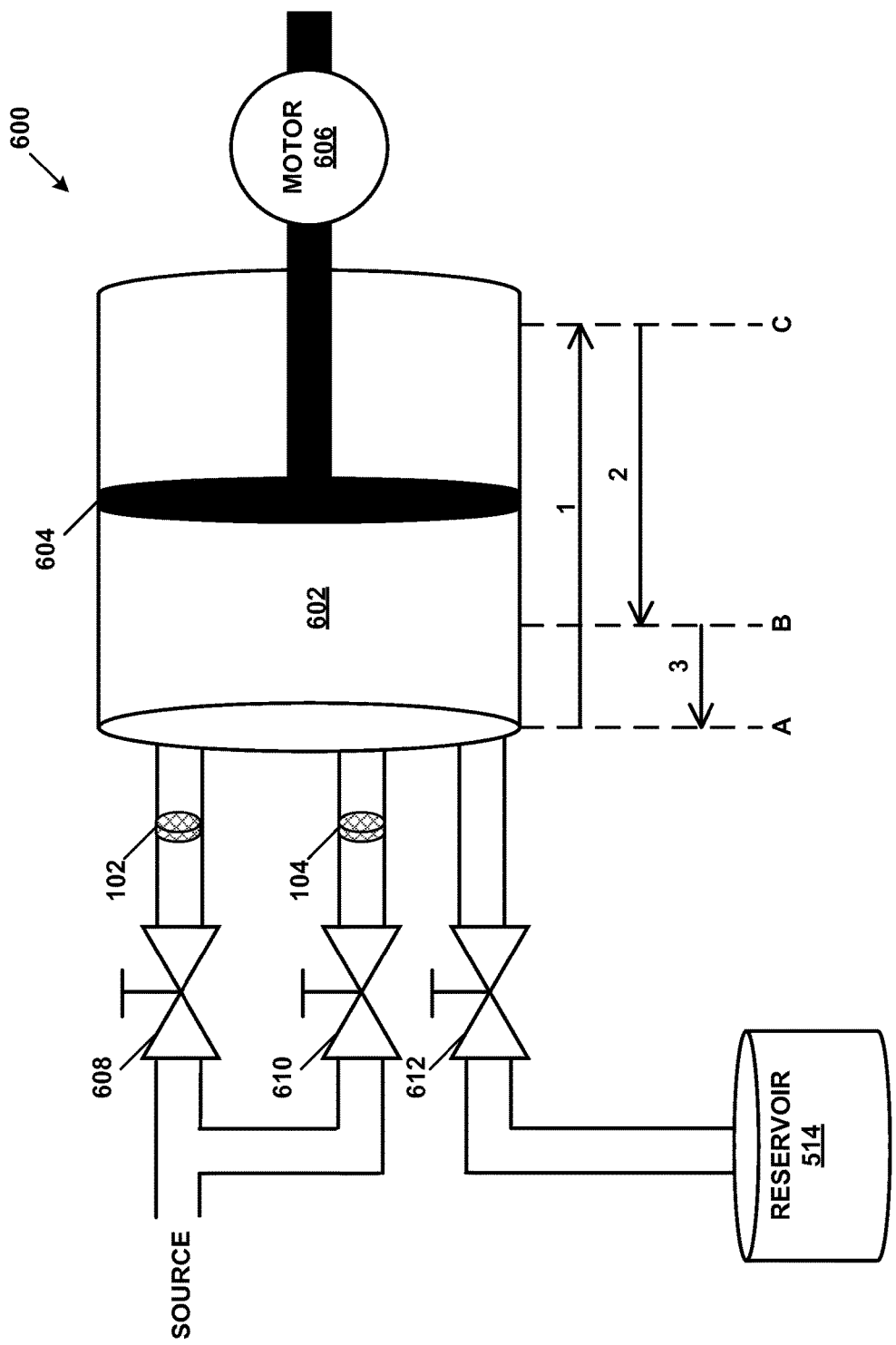
FIG. 6 is a conceptual diagram illustrating an example device for isolating a substance from a solution according to techniques of this disclosure.

FIG. 6 is a conceptual diagram illustrating an example device for isolating a substance from solution according to techniques of this disclosure. Device 600 may be configured to draw a solution from a source and return the solution to a source, wherein the returned solution does not include an isolated substance. A source may be any container containing a solution from which a substance is to be isolated. In the example where glucose is to be isolated from blood, source may be the circulatory system of a patient or an intermediate vessel containing blood drawn from a patient. Device 600 is configured to operate according to a reversible mechanical cycle.

As illustrated in FIG. 6, device 600 includes first filter 102, second filter 104, cylinder 602, piston 604, motor 606, valve 608, valve 610, valve 612, and reservoir 510. First filter 102 may be any of the example first filters described above. In the example where glucose is to be isolated from blood, first filter 102 may include a sheet of graphene including apertures sized and spaced according to the example illustrated in FIG. 3. Second filter 104 may be any of the example second filters described above. In the example where glucose is to be isolated from blood, second filter 104 may include a sheet of graphene including apertures sized and spaced according to the example illustrated in FIG. 4. As illustrated in FIG. 6, components of device are operably coupled. In one example, cylinder 602 and sections operably coupling elements may be constructed of rigid material.

As illustrated in FIG. 6, piston 604 is disposed in cylinder 602 and operably coupled to motor 606. Motor 606 is configured to cause head of piston 604 to move between position A of cylinder 602 to position C of cylinder 602 and back. Motor 606 may be any type of translation motor that causes piston 604 to move from position A to position C in a reversible manner. Valve 608, valve 610, and valve 612 are controllable valves that may opened or closed. Valve 608, valve 610, and valve 612 may be configured such that they may be opened or closed using an electrical signal. In one example, the electrical signal may be generated using a general purpose computer configured to operate according to techniques described in this disclosure. As described in detail below, device 600 is configured such that valves 608, valve 610, and valve 612 are opened and closed as piston 604 completes moves through cylinder 602 in a reversible manner such that a substance may be isolated from a solution.

Device 600 may be configured such that in an initial operational state head of piston 604 is in position A with valve 608 open and valves 610 and 612 closed. Motor 606 may cause head of piston 604 to move from position A to position C (1). Thereby drawing a solution from a source through first filter 102 and into cylinder 602. In the example where glucose is the substance to be isolated from blood first filter 102 may be configured such that objects having a size less than or equal to the size of glucose enter cylinder 602 and objects have a size larger than the size of glucose remain on the side of first filter 102 opposite cylinder 602. After cylinder 602 is filled (i.e., head of piston 602 reaches position C), valve 608 may be closed and valve 610 may be open while valve 612 remains closed. Motor 606 then causes head of piston 604 to move from position C to position B (2). Thereby causing contents of cylinder 602 to flow through second filter 104 to source. In the example where glucose is the substance to be isolated from blood second filter 104 may be configured such that objects having a size less than the size of glucose return to source and glucose remains between the opposite side of filter 104 and position B.

When head of piston 604 reaches position B, valve 610 may be closed and valve 612 may be opened and motor 606 may cause head of piston 604 to move from position B to position A. Thereby causing particles that were able to pass through first filter 102 but not able to pass through second filter 104 to be isolated in reservoir 514. As described above with respect to FIG. 5, the amount of a substance in reservoir 514 may be measured in order to determine the amount of substance that has been isolated for a solution. When the head of piston 604 returns to position A, valve 612 may be closed and valve 608 may be opened. Thereby return device 600 to the initial operation state described above.

The process of respectively opening and closing the valve 608, valve 610, and valve 612 as piston 604 moves from positions A to C to B to A may be repeated as necessary to continually isolate a substance in reservoir. Source should be continuously replenished and mixed, as fluid enters from the source through valve 608 and returns to the source through valve 610. In should be noted that position B may be adjusted during an initial calibration of device 600 so that the cylinder 602 contains few or no small objects (e.g. smaller than a substance to be isolated) before valve 610 is closed and valve 612 is opened and head of piston 604 is moved from position B to position A. In this manner, device 600 represents an example of a system configured to isolate a substance from a solution, wherein particles of the substance have an effective diameter that is within a range defined by effective diameters of a solution.

Figure 8:
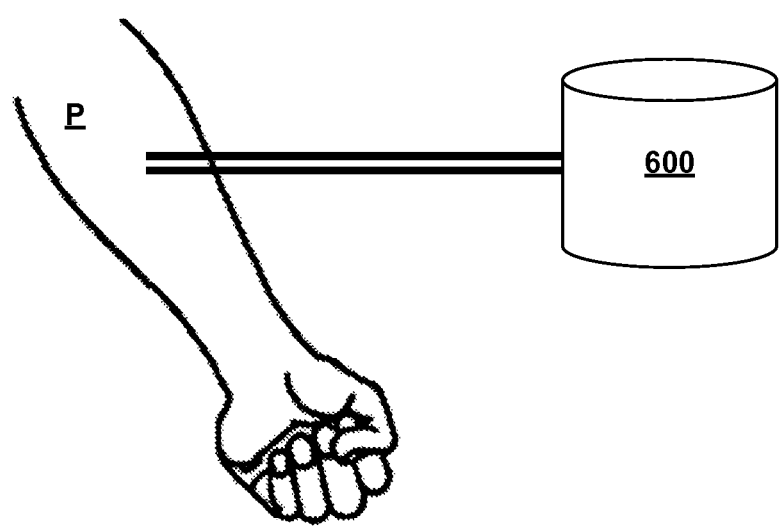
FIG. 8 is a conceptual diagram illustrating an example device for isolating a substance from blood affixed to a patient.

In some examples device 600 may be implemented as part of an external medical device or may be implemented as part of an implantable medical. FIG. 8 is a conceptual diagram illustrating an example device for isolating a substance from blood affixed to a patient. In the example illustrated in FIG. 8, device 600 is an external medical device that is operably coupled to patient P. In this manner, device 600 is an example of a device configured to isolate a substance from blood, wherein particles of the substance have an effective diameter that is within a range defined by effective diameters of constituents of blood.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belong. Although any methods and materials similar or equivalent to those described herein can also be used in the practice or testing of the disclosure, the preferred methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure are not entitled to antedate such publication by virtue of prior invention. Further, the dates of publication provided may be different from the actual publication dates which may need to be independently confirmed.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto.

Various examples have been described. These and other examples are within the scope of the following claims.

What is claimed is:

1. A method for treating diabetes, the method comprising:
   implanting into a subject in need thereof a device comprising:
   a first graphene sheet, wherein the first graphene sheet comprises a first plurality of apertures having an effective diameter that allows passage of glucose through the first graphene sheet;
   a second graphene sheet comprising a second plurality of apertures; and
   a conduit system operably coupled to the first graphene sheet and the second graphene sheet, wherein the conduit system is configured to isolate glucose,
   wherein the device is effective for lowering the amount of glucose in a bloodstream.

2. The method of claim 1, wherein the first plurality of apertures comprises apertures with a nominal diameter of at least 0.74 nm and 2-3% larger than the effective diameter of glucose.

3. The method of claim 1, wherein the first plurality of apertures comprises apertures that are nominally spaced 2 nanometers center-to-center.

4. The method of claim 1, wherein the device is configured to allo blood to cross the first graphene sheet and the second graphene sheet.

5. The method of claim 1, further comprising circulating blood through the first graphene sheet and the second graphene sheet.

6. The method of claim 1, wherein the glucose in the bloodstream is lowered by non-hormonal means.

7. A method for isolating blood constituents, the method comprising:
   passing blood through a first graphene sheet comprising a first plurality of apertures and a second graphene sheet comprising a second plurality of apertures, wherein the first plurality of apertures and the second plurality of apertures comprise apertures with an effective diameter that allows passage of the blood constituents through the first graphene sheet and the second graphene sheet to thereby isolate the blood constituents from the blood wherein a conduit system is operably coupled to the first graphene sheet and the second graphene sheet, wherein the conduit system is configured to isolate glucose, and wherein the blood constituents comprise glucose.

8. The method of claim 7, wherein the first plurality of apertures comprises apertures with a nominal diameter of at least 0.74 nm and 2-3% larger than the effective diameter of glucose.

9. The method of claim 7, wherein the first plurality of apertures comprises apertures that are nominally spaced 2 nanometers center-to-center.

10. The method of claim 7, wherein a circulatory system circulates blood through the first graphene sheet and the second graphene sheet.

11. The method of claim 7, wherein the method lowers the amount of glucose in the bloodstream of a subject.

12. The method of claim 7, where the blood constituents further comprise one or more of sucrose, polyethylene glycol, inulin, myoglobin, lysozyme, lactoglobulin, egg albumin, hemoglobin, and serum albumin.

13. The method of claim 7, further comprising returning at least some of the isolated blood constituents to the blood.

14. The method of claim 7, wherein the first graphene sheet and the second graphene sheet are a part of a medical device implanted in a subject.

* * * * *